(12) United States Patent
Sperling et al.

(10) Patent No.: US 10,745,686 B2
(45) Date of Patent: Aug. 18, 2020

(54) METHOD FOR SEPARATING DNA BY SIZE

(71) Applicant: QIAGEN GmbH, Hilden (DE)

(72) Inventors: Tanya Sperling, Hilden (DE); Nicola Scholle, Hilden (DE); Thorsten Singer, Hilden (DE); Margit Hiesinger, Hilden (DE)

(73) Assignee: QIAGEN GmBH, Hilden (DE)

( * ) Notice: Subject to any disclaimer, the term of this patent is extended or adjusted under 35 U.S.C. 154(b) by 349 days.

(21) Appl. No.: 14/764,045

(22) PCT Filed: Feb. 7, 2014

(86) PCT No.: PCT/EP2014/052480
§ 371 (c)(1),
(2) Date: Jul. 28, 2015

(87) PCT Pub. No.: WO2014/122288
PCT Pub. Date: Aug. 14, 2014

(65) Prior Publication Data
US 2016/0024490 A1    Jan. 28, 2016

Related U.S. Application Data

(60) Provisional application No. 61/762,674, filed on Feb. 8, 2013.

(30) Foreign Application Priority Data

Feb. 8, 2013  (EP) ..................... 13154732

(51) Int. Cl.
| | | |
|---|---|---|
| C12N 15/10 | (2006.01) | |
| C12Q 1/6806 | (2018.01) | |
| C12Q 1/6869 | (2018.01) | |
| G01N 33/50 | (2006.01) | |

(52) U.S. Cl.
CPC ..... C12N 15/1003 (2013.01); C12N 15/1017 (2013.01); C12Q 1/6806 (2013.01); C12Q 1/6869 (2013.01)

(58) Field of Classification Search
CPC ............ C12N 15/1017; C12N 15/1003; C12Q 2525/204
See application file for complete search history.

(56) References Cited

U.S. PATENT DOCUMENTS

| | | | |
|---|---|---|---|
| 5,234,809 A * | 8/1993 | Boom | C07H 21/00 422/504 |
| 5,705,628 A | 1/1998 | Hawkins | |
| 5,898,071 A | 4/1999 | Hawkins | |
| 6,037,465 A | 3/2000 | Hillebrand et al. | |
| 6,383,393 B1 * | 5/2002 | Colpan | C12N 15/101 210/198.2 |
| 6,534,262 B1 | 3/2003 | McKernan et al. | |
| 6,699,987 B2 | 3/2004 | Hillebrand et al. | |
| 7,022,835 B1 | 4/2006 | Rauth et al. | |
| 7,741,463 B2 | 6/2010 | Gormley et al. | |
| 8,153,375 B2 | 4/2012 | Travers et al. | |
| 8,309,330 B2 | 11/2012 | Travers et al. | |
| 8,455,193 B2 | 6/2013 | Travers et al. | |
| 8,563,478 B2 | 10/2013 | Gormley et al. | |
| 9,376,678 B2 | 6/2016 | Gormley et al. | |
| 9,404,146 B2 | 8/2016 | Travers et al. | |
| 9,542,527 B2 | 1/2017 | Travers et al. | |
| 9,582,640 B2 | 2/2017 | Travers et al. | |
| 2001/0041332 A1 | 11/2001 | Hillebrand et al. | |
| 2007/0249821 A1 * | 10/2007 | Bitner | C07H 21/00 536/25.4 |
| 2009/0298075 A1 | 12/2009 | Travers et al. | |
| 2016/0355880 A1 | 12/2016 | Gormely et al. | |

FOREIGN PATENT DOCUMENTS

| | | |
|---|---|---|
| CA | 2 597 573 A1 | 8/2006 |
| DE | 198 56 064 A1 | 6/2000 |
| DE | 199 43 374 A1 | 3/2001 |
| EP | 0 343 934 A2 | 11/1989 |
| EP | 0 389 063 A2 | 9/1990 |
| EP | 0 757 106 A2 | 2/1997 |
| EP | 1 260 595 A2 | 11/2002 |
| WO | 96/41811 A1 | 12/1996 |
| WO | 98/31461 A1 | 7/1998 |
| WO | 98/31840 A1 | 7/1998 |

(Continued)

OTHER PUBLICATIONS

"Biological Buffers", AppliChem, pp. 1-20 (Year: 2008).*

(Continued)

*Primary Examiner* — Teresa E Strzelecka
(74) *Attorney, Agent, or Firm* — Seed IP Law Group LLP

(57) ABSTRACT

The present invention provides method for isolating DNA molecules having a size above a certain cut-off value from a DNA containing sample, comprising a) contacting the sample with a binding buffer which comprises a chaotropic agent and a buffering agent to provide a binding mixture and binding DNA molecules having a size above the cut-off value to a binding matrix which has a silicon containing surface, wherein the cut-off value is determined by the pH value of the binding mixture; b) separating the bound DNA from the remaining sample; c) optionally washing the bound DNA; and d) optionally eluting the bound DNA from the binding matrix. Said method allows the size selective purification of DNA molecules.

43 Claims, 8 Drawing Sheets

(56) References Cited

FOREIGN PATENT DOCUMENTS

| WO | 99/58664 A1 | 11/1999 |
|---|---|---|
| WO | 01/71732 A2 | 9/2001 |
| WO | 03/004150 A1 | 1/2003 |
| WO | 03/057910 A2 | 7/2003 |
| WO | 03/080834 A2 | 10/2003 |
| WO | 2004/003231 A2 | 1/2004 |
| WO | 2006/084753 A1 | 8/2006 |
| WO | 2008/002725 A2 | 1/2008 |
| WO | 2012/003374 A2 | 1/2012 |
| WO | 2014/122288 A1 | 8/2014 |

OTHER PUBLICATIONS

DeAngelis et al., "Solid-phase reversible immobilization for the isolation of PCR products," *Nucleic Acids Research* 23(22):4742-4743 (1995).

Guo et al., "DNA Extraction Procedures Meaningfully Influence q-PCR-Based mtDNA Copy Number Determination," *Mitochondrion* 9(4):261-265 (Jul. 2009).

Lis et al., "Size fractionation of double-stranded DNA by precipitation with polyethylene glycol," *Nucleic Acids Research* 2(3):383-395 (Mar. 1975).

Metzker, "Sequencing technologies—the next generation," *Nature Reviews | Genetics* 11:31-46 (Jan. 2010).

Nanassy et al., "Capture of genomic DNA on glass microscope slides," *Anal Biochem.* 365(2):240-245 (Jun. 15, 2007).

Voelkerding et al., "Next-Generation Sequencing: From Basic Research to Diagnostics," *Clinical Chemistry* 55(4):641-658 (2009).

Paithankar et al., "Precipitation of DNA by polyethylene glycol and ethanol," Nucleic Acids Res. 19(6): 1346, 1 page, (1991).

Stein et al., "An efficient method to assemble linear DNA templates for in vitro screening and selection systems," Nucleic Acids Res. 37(18): e122, 9 pages, (2009).

Prodelalova et al., "Isolation of genomic DNA using magnetic cobalt ferrite and silica particles," *Journal of Chromatography A* 1056:43-48 (2004).

Engelstein et al., "An Efficient, Automatable Template Preparation for High Throughput Sequencing," Microbial & Comparative Genomics 3(4):237-241 (1998).

Zhang et al., "Preparation of Porous Magnetic Silica Microspheres and Their Application in Genomic Deoxyribonucleic Acids Extraction," Chinese Journal of Analytical Chemistry 34(7):923-926 (5 pages) (Jul. 2006).

\* cited by examiner

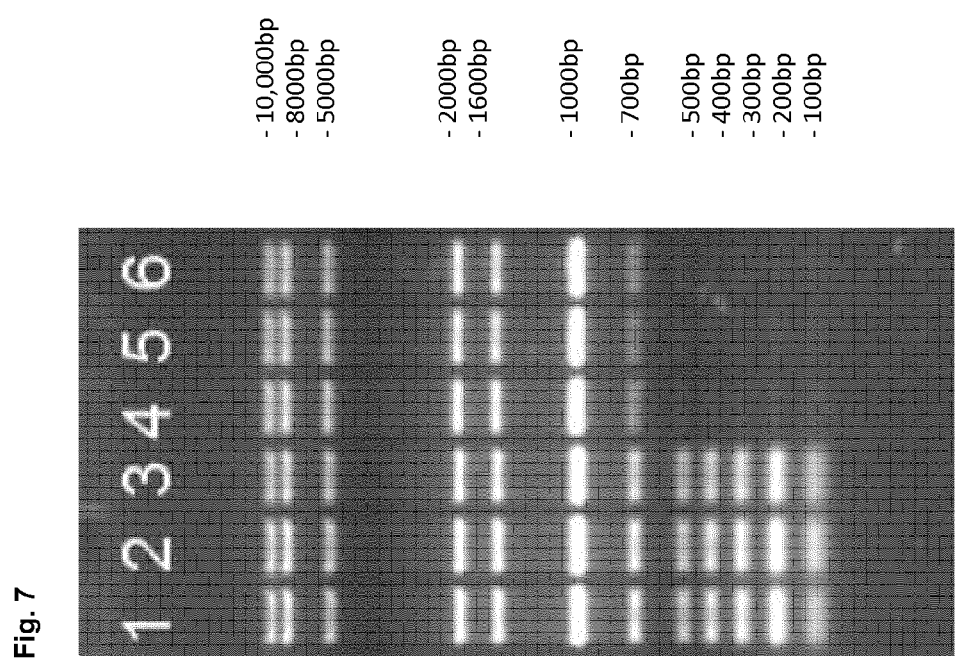

METHOD FOR SEPARATING DNA BY SIZE

FIELD OF INVENTION

The present invention provides methods suitable for size selective isolation of DNA molecules. The methods of the present invention are particularly useful in order to isolate DNA molecules having a desired minimum length during the preparation of a sequencing library. Furthermore, kits are provided that allow the size selective isolation of DNA molecules.

BACKGROUND OF THE INVENTION

Different methods for isolating nucleic acids are well-known in the prior art. Such methods involve separating nucleic acids of interest from other sample components, such as for example protein contaminations or potentially also other nucleic acids, also often referred to as non-target nucleic acids. E.g. methods for isolating nucleic acids such as DNA from various sample materials by binding them to a silica material in the presence of a chaotropic salt are well-known and established in the prior art. Exemplary methods that are based on said principle are e.g. described in EP 0 389 063, WO 03/057910, EP 0 757 106, U.S. Pat. No. 6,037,465 and WO 2006/084753.

If it is intended to isolate a specific nucleic acid of interest from other nucleic acids the separation process is usually based on differences in parameters of the target and the non-target nucleic acid such as for example their topology (for example super-coiled DNA from linear DNA), their size (length) or chemical differences (e.g. DNA from RNA) and the like.

For certain applications differences in the size is an important criterion to distinguish target nucleic acids from non-target nucleic acids. E.g. size selective fractionation of DNA is an important step in the library construction for next generation sequencing (NGS) applications. Different NGS technologies and methods exist such as pyrosequencing, sequencing by synthesis or sequencing by ligation. Most NGS platforms share a common technological feature, namely the massively parallel sequencing of clonally amplified or single DNA molecules that are spatially separated in a flow cell or by generation of an oil-water emulsion.

In NGS, sequencing is performed by repeated cycles of polymerase-mediated nucleotide extensions or, in one format, by iterative cycles of oligonucleotide ligation. As a massively parallel process, NGS generates hundreds of megabases to gigabases of nucleotide-sequence output in a single instrument run, depending on the platform. The inexpensive production of large volumes of sequence data is the primary advantage over conventional methods. Therefore, NGS technologies have become a major driving force in genetic research. Several NGS technology platforms have found widespread use and include, for example, the following NGS platforms: Roche/454, Illumina Solexa Genome Analyzer, the Applied Biosystems SOLiD™ system, Ion Torrent™ semiconductor sequence analyzer, PacBio® real-time sequencing and Helicos™ Single Molecule Sequencing (SMS). NGS technologies, NGS platforms and common applications/fields for NGS technologies are e.g. reviewed in Voelkerding et al (Clinical Chemistry 55:4 641-658, 2009) and Metzker (Nature Reviews/Genetics Volume 11, January 2010, pages 31-46).

Besides the feature that sequencing is performed in a massively parallel manner in NGS technologies, NGS technology platforms have in common that they require the preparation of a sequencing library which is suitable for massive parallel sequencing. Examples of such sequencing libraries include fragment libraries, mate-paired libraries or barcoded fragment libraries. Most platforms adhere to a common library preparation procedure with minor modifications before a "run" on the instrument. This procedure includes fragmenting the DNA (which may also be obtained from cDNA), e.g. by mechanical shearing, such as sonification, hydro-shearing, ultrasound, nebulization or enzymatic fragmentation followed by DNA repair and end polishing (blunt end or A overhang) and, finally, platform-specific adaptor ligation. The preparation and design of such sequencing libraries is also described e.g. in Voelkerding, 2009 and Metzker, 2010.

In order to ensure high quality sequencing data, efficient library preparation-methods are needed. Furthermore, to reduce the background in the sequencing reads, it is important to remove DNA contaminants that might be present in the sequence library as a result of the library preparation. An example of such DNA contaminants are adapter monomers and adapter-adapter ligation products that are often present in the sequencing library after adapter ligation. These contaminating small DNA molecules must be removed prior to sequencing.

To ensure efficient adaptor ligation, adaptors are used in excess during adapter ligation. Thus, after adapter ligation, unligated adaptor monomers and adaptor-adaptor ligation products such as adapter dimers are present in addition to the adaptor ligated DNA molecules. It is important to remove unligated adaptor monomers and adaptor-adaptor ligation products from the adaptor ligated DNA molecules. Otherwise, unligated adaptor monomers and adaptor-adaptor ligation products will use up sequencing capacity, thereby diminishing the power available to investigate sequences of interest. If the sequencing library comprises considerable amounts of unligated adapter monomers and adapter dimers, valuable sequencing resources are wasted. Therefore, removing unligated adaptor monomers and adaptor-adaptor ligation products increases the value of the downstream sequencing. Unligated adaptor monomers and adaptor-adaptor ligation products are usually removed by a size selective purification of the larger adaptor ligated DNA molecules, which contain the DNA fragments to be sequenced.

Several approaches were developed in the prior art in order to isolate DNA of a specific target size, respectively a specific target size range. These size selection methods can be used in order to remove adapter dimers and monomers, as these DNA contaminations have a size that is smaller than the adapter ligated DNA molecules. A classic method for isolating DNA of a target size involves the separation of the DNA in a gel, cutting out the desired gel band(s) and then isolating the DNA of the target size from the gel fragment(s). Respective gel based size selection methods are often recommended in many next generations sequencing library preparation protocols in order to remove adapter monomers and dimers. However, respective methods are time consuming, as the portion of the gel containing the nucleic acids of interest must be manually cut out and then treated to degrade the gel or otherwise extract the DNA of the target size from the gel slice.

Another widely used technology is the size selective precipitation with polyethylene glycol based buffers (Lis and Schleif Nucleic Acids Res. 1975 March; 2(3):383-9) or the binding/precipitation on carboxyl-functionalized beads (DeAngelis et al, Nuc. Acid. Res. 1995, Vol 23(22), 4742-3; U.S. Pat. Nos. 5,898,071 and 5,705,628, commercialized by Beckman-Coulter (AmPure XP; SPRIselect) and U.S. Pat.

No. 6,534,262). Even if it has been established as the "gold standard" in size selection in NGS, the procedure is time consuming and cumbersome especially when doing it manually. Polyethylene glycol based isolation methods are in particular disadvantageous because of the highly viscous polyethylene glycol which may hamper efficient washing. In addition there is a risk of bead carry-over which may have a disadvantageous impact on downstream reactions such as e.g. subsequent enzymatic reactions. Size selection methods that are based on the use of titratable anion exchange compositions and pH gradients are described e.g. in WO 03/080834.

The prior art shows that there is an increasing interest and need for methods allowing the size selective isolation of DNA molecules, in particular of DNA molecules having a certain minimum size. In particular, there is a need for simple, efficient methods for isolating DNA of a specific minimum size that can be integrated into existing next generation sequencing library preparation protocols. Furthermore, there is a need for fast, simple and reliable methods for removing unligated adapter monomers and adapter dimers from adapter ligation samples, in particular adapter ligation samples obtained in the preparation of a sequencing library.

Therefore, it is an object of the present invention to provide a method for isolating DNA of a target size or a target size range from a sample comprising DNA molecules of different sizes. In particular, it is the object of the present invention to provide a method that allows to separate adapter ligated DNA molecules from unligated adapter monomers and adapter-adapter ligation products based on the larger size of the adapter ligated DNA molecules. In particular, it is an object to provide respective methods that are fast, reliable and can be integrated into the work-flow of next generation sequencing library preparation protocols.

SUMMARY OF THE INVENTION

The present invention is based on the established DNA isolation technology, wherein DNA is bound to a silicon containing surface of a binding matrix in the presence of a chaotropic salt. The inventors now surprisingly found that the size of DNA molecules that bind to the binding matrix can be controlled by the pH value of the binding mixture. This finding allows a precise size selective binding by appropriate choice of the binding pH value. In the method according to the present invention, the pH value used during binding determines the size of the DNA that is bound to the binding matrix and accordingly, determines the size of the DNA that is recovered by the method according to the present invention. I.e. the binding pH value determines the cut-off value and thus determines the size of the recovered DNA, respectively determines the size of the DNA that is not bound and thus is removed during the isolation process. The higher the binding pH value the greater the lower size limit of the bound and thus recovered DNA molecules.

Based on this finding the present invention provides according to a first aspect a method for isolating DNA molecules having a size above a certain cut-off value from a DNA containing sample, wherein said method comprises
 a) contacting the sample with a binding buffer which comprises a chaotropic salt and a buffering agent to provide a binding mixture and binding DNA molecules having a size above the cut-off value to a binding matrix which has a silicon containing surface, wherein the cut-off value is determined by the pH value of the binding mixture;
 b) separating the bound DNA from the remaining sample;
 c) optionally washing the bound DNA; and
 d) optionally eluting the bound DNA from the binding matrix.

In said method, DNA molecules having a size above the desired cut-off value efficiently bind to the binding matrix while DNA molecules having a size below said cut-off value are predominantly not bound and thus are not recovered by said method. Thereby, DNA molecules shorter than the cut-off value can be efficiently and reliably removed and DNA molecules having a desired target size are enriched. The pH value used during binding determines the cut-off value and thus determines the lower size limit of the recovered DNA molecules. As is shown by the examples, the method according to the invention enables a precise size selection based on variations in the binding pH value.

According to a second aspect, a method is provided for isolating adapter ligated DNA molecules from an adapter ligation sample and for removing adapter monomers and adapter-adapter ligation products, wherein adapter ligated DNA molecules are separated from unligated adapter monomers and adapter-adapter ligation products based on the larger size of the adapter ligated DNA molecules, wherein said method comprises
 a) contacting the adapter ligation sample with a binding buffer which comprises a chaotropic salt and a buffering agent to provide a binding mixture and binding adapter ligated DNA molecules to a binding matrix which has a silicon containing surface, wherein under the used binding conditions adapter monomers and adapter-adapter ligation products substantially do not bind to the binding matrix and wherein the cut-off value is determined by the pH value of the binding mixture;
 b) separating the bound DNA from the remaining sample;
 c) optionally washing the bound DNA; and
 d) optionally eluting the bound DNA from the binding matrix.

Said method is a specific embodiment of the method according to the first aspect. Here, the size selection method according to the present invention is used in order to separate desired adapter ligated DNA molecules from unwanted adapter monomers and adapter-adapter ligation products such as in particular adapter dimers. The method can be well integrated in existing work-flows for preparing next generation sequencing libraries as therein, adapter ligation steps are usually performed. Said method reliably removes unligated adapters and adapter-adapter ligation products such as adapter dimers because these contaminating DNA molecules are shorter than the adapter ligated DNA molecules. The pH value used during binding again determines the cut-off value and thus determines the size of the DNA molecules that are recovered during isolation. The cut-off value is chosen such that unligated adapter monomers and adapter-adapter-ligation products of the expected size are below the cut-off value and thus are substantially not bound in the size selective binding step.

According to a third aspect, a kit is provided for the selective binding of DNA molecules having a size above a desired cut-off value, comprising
 a) a binding buffer comprising a chaotropic salt and a buffering agent, wherein the binding buffer has a defined pH value that allows binding of DNA molecules having a size above a desired cut-off value when mixed with a DNA containing sample;
 b) a binding matrix having a silicon containing surface;
 c) optionally a washing solution; and
 d) optionally an elution solution.

A respective kit can be advantageously used in conjunction with and for performing the methods according to the first and second aspect of the invention.

Other objects, features, advantages and aspects of the present application will become apparent to those skilled in the art from the following description and appended claims. It should be understood, however, that the following description, appended claims, and specific examples, while indicating preferred embodiments of the application, are given by way of illustration only. Various changes and modifications within the spirit and scope of the disclosed invention will become readily apparent to those skilled in the art from reading the following.

FIGURES

FIG. 1 shows a electropherogram of Covaris-sheared fragmented DNA before and after size selective purification according to the invention with pH 7.4, pH 7.8 or pH 8.0 as binding pH (see example 1). The curves demonstrates the pH dependent removal of DNA fragments smaller than 50 bp (pH 7.4), 100 bp (pH 7.8) and 150 bp (pH 8.0). FU: fluorescence units.

FIGS. 2 and 3 show the results of size selection after end-repair (upper curve) and after adapter ligation (lower curve) using a size selection approach according to the invention (FIG. 2) or using a prior art method that is based on the use of carboxylated AMPure beads and PEG (FIG. 3) (see example 2). In FIGS. 2 to and 3, the two runs were combined in one figure. Therefore, the X-axis indicates the retention time in [s]. To simplify the determination of the DNA size, a corresponding curve indicating the size in [bp] is shown below the diagrams.

FIG. 4 shows adapter reads in % of total library-reads from three independent libraries per used size selection method (see example 2).

FIG. 5 shows in the large image the size distribution after adapter ligation that is obtained if no size selection step is performed in order to remove adapter monomers and dimers. As can be seen, adapter monomers and dimers are present in large amounts in the adapter ligation sample. Therefore, it is important to remove them by size selection. A scaled up image of the data showing the correct size distribution of Illumina compatible library fragments following size selection according to the invention is shown in the insert. In the insert, the X-axis shows the same [bp] scale as the large figure. The Y-axis reads regarding the FU values (from bottom to top: 0, 50, 100, 150, 200 and 250).

FIG. 7 shows the size selective isolation of DNA fragments of a DNA Molecular Weight Marker at different binding buffer pH-values: 1-3: pH 7; 4-7: pH 7.5 (see example 4).

DETAILED DESCRIPTION OF THE INVENTION

Figure 1:
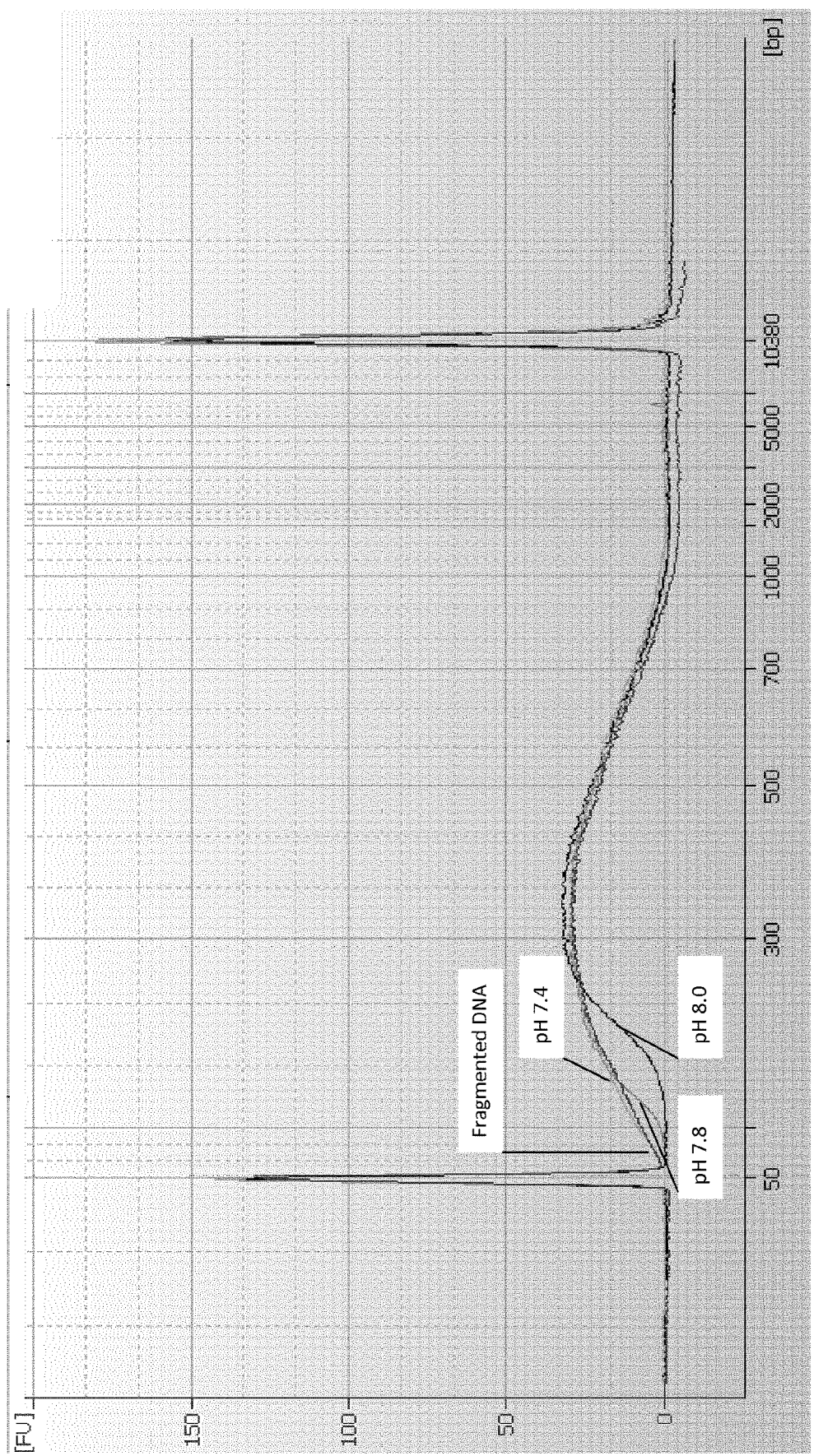

The present invention provides methods allowing the isolation of DNA molecules by size from a sample comprising DNA molecules of different sizes. The pH value used during binding determines the size of the DNA molecules that are bound to the silica binding matrix in the presence of a chaotropic salt. The present invention allows to isolate DNA molecules of a pre-determined minimum size by appropriate choice or adjustment of the binding pH value. It was found for chaotropic salts such as guanidinium salts that an increase in the binding pH value increases the cut-off value and thus increases the size of the DNA molecules that are recovered. For other chaotropic salts such as $CaCl_2$, the pH dependent effect was reversed, i.e. an increase in the binding pH decreased the cut-off value and thus decreased the size of the DNA molecules that are recovered. DNA molecules having a size below the cut-off value are not bound in the size selective binding step and thus are depleted. Thus, by appropriate choice of the binding pH value it is possible to precisely adjust the cut-off value and accordingly, it is possible to precisely adjust and thus control the minimum size of the DNA molecules that are isolated using the method according to the present invention. This observed pH dependency which allows a precise size selection even when using the same type and concentration of chaotropic salt was unexpected. The method of the invention is fast, reliable and can be automated.

According to a first aspect a method for isolating DNA molecules having a size above a certain cut-off value from a DNA containing sample is provided, wherein said method comprises a) contacting the sample with a binding buffer which comprises a chaotropic salt and a buffering agent to provide a binding mixture and binding DNA molecules having a size above the cut-off value to a binding matrix which has a silicon containing surface, wherein the cut-off value is determined by the pH value of the binding mixture;

b) separating the bound DNA from the remaining sample;

c) optionally washing the bound DNA; and d) optionally eluting the bound DNA from the binding matrix.

According to a second, related aspect, a method is provided for isolating adapter ligated DNA molecules from an adapter ligation sample and for removing adapter monomers and adapter-adapter ligation products, wherein adapter ligated DNA molecules are separated from unligated adapter monomers and adapter-adapter ligation products based on the larger size of the adapter ligated DNA molecules, wherein said method comprises a) contacting the adapter ligation sample with a binding buffer which comprises a chaotropic salt and a buffering agent to provide a binding mixture and binding adapter ligated DNA molecules to a binding matrix which has a silicon containing surface, wherein under the used binding conditions adapter monomers and adapter-adapter ligation products substantially do not bind to the binding matrix and wherein the cut-off value for binding is determined by the pH value of the binding mixture;

b) separating the bound DNA from the remaining sample;

c) optionally washing the bound DNA; and d) optionally eluting the bound DNA from the binding matrix.

d) optionally eluting the bound DNA from the binding matrix.

As described above, the method according to the second aspect is a preferred embodiment of the method according to the first aspect. The method is in particular suitable for size selection during preparation of a sequencing library suitable for next generation sequencing. The individual steps a) to d) as well as non-limiting suitable and preferred embodiments will now be described in detail.

Step a)

In step a), the DNA containing sample is contacted with a binding buffer which comprises a chaotropic salt and a buffering agent to provide a binding mixture. In step a), DNA molecules having a size above the cut-off value efficiently adsorb to the binding matrix while smaller DNA molecules having a size below the cut-off value and contaminants present in the sample substantially do not bind.

The DNA containing sample comprises DNA molecules of different sizes (lengths). The DNA containing sample may comprise single-stranded and/or double stranded DNA. The method according to the present invention allows size selection of single stranded as well as of double-stranded DNA. Preferably, the DNA molecules are linear, double-stranded DNA molecules. The DNA containing sample can be of various origins, including biological samples and artificial samples that were obtained during nucleic acid processing. According to one embodiment, the DNA containing sample is a sample of extracted DNA or extracted DNA that has been further processed, e.g. by shearing or by way of an enzymatic reaction. According to one embodiment, the DNA containing sample was obtained after an enzymatic reaction. Exemplary enzymatic reactions that provide DNA containing samples that can be processed using the methods of the invention include but are not limited to amplification reactions, ligase reactions, in particular adapter ligation reactions and polynucleotide, e.g. poly A, tailing reactions According to one embodiment, the DNA containing sample comprises fragmented DNA, e.g. sheared DNA. According to one embodiment, the DNA containing sample comprises sheared genomic DNA or sheared cDNA. Thus, according to one embodiment the DNA containing sample is a solution resulting from a size shearing procedure. Such DNA containing sample comprises DNA fragments of different sizes. Said fragmented DNA can be end-repaired to provide DNA fragments having blunt ends. Thus, according to one embodiment, the DNA containing sample comprises linear, blunt-ended DNA fragments of different sizes. According to one embodiment, the DNA containing sample was obtained during the preparation of a sequencing library, in particular during preparation of a next generation sequencing library. According to one embodiment, the DNA containing sample comprises amplification products, e.g. PCR products. Thus, according to one embodiment, the DNA containing sample is a solution resulting from an amplification procedure, in particular resulting from a PCR amplification. According to one embodiment, the DNA containing sample is an adapter ligation sample that was obtained as a result of an adapter ligation step. According to a preferred embodiment, the DNA containing sample is an adapter ligation sample which comprises (i) double-stranded DNA molecules that are flanked 5' and/or 3' by adapters, (ii) adapter monomers and (iii) adapter-adapter ligation products such as e.g. adapter dimers. Furthermore, the DNA containing sample may comprise additional contaminating components such as e.g. mono, oligo- and/or polynucleotides and proteins such as enzymes that are e.g. still present in the DNA containing sample from previous enzymatic sequencing library processing steps. The method according to the present invention allows to size selectively purify double-stranded DNA molecules that are flanked 5' and/or 3' by adapters, preferably are flanked at their 5' end and their 3' end by adapters, thereby efficiently removing respective contaminants.

To provide a binding mixture, the DNA containing sample is contacted with a binding buffer which comprises a chaotropic salt and a buffering agent. Preferably, the binding conditions are exclusively established by the binding buffer. Therefore, preferably, the size selective binding conditions are exclusively determined by the binding buffer. Of particular importance is the binding pH value as it determines the cut-off value for size selection. It is preferred that after contacting the binding buffer with the DNA containing sample, a pH value is provided in the resulting binding mixture that corresponds to or substantially corresponds to the pH value of the binding buffer. Thus, preferably, the pH value of the binding buffer is substantially maintained in the resulting binding mixture. This is achieved, respectively is supported by the buffering agent that is used in the binding buffer. Preferably, the pH value in the binding mixture does not deviate by more than +/−0.2 pH units, preferably not more than +/−0.15 pH units, more preferred not more than +/−0.1 pH units, most preferred not more than +/−0.05 pH units from the pH value of the binding buffer.

Hence, the binding conditions can be and preferably are controlled by the binding buffer and the binding conditions such as the concentration of the chaotropic salt and in particular the binding pH value required for size selection are established by contacting the DNA containing sample with the binding buffer. Preferably, no further adjustments are made to establish the binding mixture. Thus, preferably, the binding mixture and the binding pH value is provided exclusively by contacting the binding buffer with the DNA containing sample. This advantageously avoids handling and adjustment errors. E.g. 1 volume of DNA containing sample can be contacted with 1 to 10, preferably 1.5 to 8, 2 to 7, 2.5 to 6, 3 to 5.5 or with 3.5 to 5 volumes of binding buffer. A ratio of 1 volume DNA containing sample to 4 volumes binding buffer is particularly preferred. Contacting the binding buffer with the sample reduces the concentration of chaotropic salt in the resulting binding mixture due to a dilution effect. Thus, the concentration of the chaotropic salt in the binding buffer must be chosen such that in the resulting binding mixture, DNA molecules having a size above the cut-off value (adjusted by the binding pH value) efficiently bind to the surface of the binding matrix.

Even though it is preferred for many applications that the pH in the binding mixture is established by contacting the DNA containing sample with the binding buffer and wherein preferably, the pH value of the binding mixture corresponds to the pH value of the binding buffer, the present invention also covers embodiments, wherein the pH value in the binding mixture is adjusted and thus modified after the DNA containing sample was contacted with the binding buffer. Thus, according to one embodiment, the pH value of the binding mixture is adjusted to the binding pH value that provides the desired cut-off value. E.g. the adjustment can be made manually. Here, e.g., the pH value of the binding mixture can be determined and then adjusted to the desired binding pH value by adding appropriate pH modifying substances such as acids or bases.

According to one embodiment, the binding mixture is obtained by contacting the DNA containing sample with the binding buffer and one or more additional buffers. Said one or more additional buffers have a pH value that differ(s) from the pH value of the binding buffer. This allows to establish a desired pH value in the binding mixture e.g. by mixing the different buffers having different pH values in certain ratios. E.g. a certain volume of the DNA containing sample is mixed in a certain ratio with the binding buffer and one or more additional buffers. This allows the flexible adjustment of the binding pH value and hence the cut-off value by mixing a certain volume of the binding buffer and a certain volume of the one or more additional buffers having a pH value different from the binding buffer with the DNA containing sample. According to one embodiment, the pH value that is established in the binding mixture due to contacting the DNA containing sample with the binding buffer and the one or more additional buffers differs from the pH value of the binding buffer and the pH value of the one or more additional buffers. According to one embodiment, no additional manual adjustments of the pH value are performed in the binding mixture. According to one embodiment, the additional buffers are binding buffers comprising a chaotropic salt and a buffering agent as described herein. According to one embodiment, the method comprises providing a set of two or more binding buffers, wherein each binding buffer comprises a chaotropic salt and a buffering agent and wherein each binding buffer has a different pH value and provides a different, defined pH value and thus cut-off value in the binding mixture. From said set of binding buffers, the user may choose the appropriate binding buffer which provides the desired cut-off value by adjusting the appropriate binding pH value in the binding mixture. Thus, according to one embodiment, the binding buffers comprise the same chaotropic salt in the same concentration. According to one embodiment, said one or more additional binding buffers, respectively the binding buffers provided in the set, comprise the same chaotropic salt in the same concentration and but differ in their pH value. Depending on the pH value, said binding buffers may comprise the same or a different buffering agent. According to one embodiment, said one or more additional binding buffers have the same composition as the binding buffer and only differ in their pH value. According to one embodiment, the pH value of the one or more additional buffers, respectively binding buffers differs by at least 0.1 pH units, at least 0.2 pH units, at least 0.3 pH units, at least 0.4 pH units, at least 0.5 pH units, at least 0.6 pH units, at least 0.7 pH units, at least 0.75 pH units, at least 0.8 pH units, at least 0.9 pH units, at least 1.0 pH units, at least 1.1 pH units, at least 1.2 pH units, at least 1.3 pH units, at least 1.4 pH units or by at least 1.5 pH units.

The chaotropic salt comprised in the binding buffer promotes binding of the DNA to the siliceous binding matrix. Chaotropic salts known to be able to promote binding of DNA to a siliceous binding matrix include but are not limited to chaotropic salts comprising a chaotropic ion such as guanidinium, thiocyanate, isothiocyanate, perchlorate, iodide, bromide, trichloroacetate and/or trifluoroacetate. Furthermore, a calcium salt such as $CaCl_2$ can be used as chaotropic salt as is demonstrated by the examples. The chaotropic salt used allows a pH dependent binding effect such that the pH value of the binding mixture determines the cut-off value as is described herein. According to one embodiment, the chaotropic salt is a guanidinium salt. Guanidinium salts include e.g. guanidinium hydrochloride, guanidinium thiocyanate, guanidinium isothiocyanate, guanidinium acetate, guanidinium phosphate, guanidinium sulphate and guanidinium carbonate. Examples of chaotropic iodide salts include but are not limited to sodium iodide, potassium iodide and the like. Examples of chaotropic perchlorate salts include sodium perchlorate, potassium perchlorate, lithium perchlorate and ammonium perchlorate. Examples of chaotropic (iso)thiocyanate salts include guanidinium (iso)thiocyanate, sodium (iso)thiocyanate, potassium(iso)thiocyanate and ammonium (iso)thiocyanate. As calcium salt, in particular $CaCl_2$ can be used as is demonstrated by the examples. Also a mixture of chaotropic salts can be used in the binding buffer. According to one embodiment, a chaotropic salt is used which comprises a chaotropic anion and a chaotropic cation as is e.g. the case with guanidinium (iso)thiocyanate.

Preferably, a guandinium salt is used as chaotropic salt. It was found that guanidinium salts are particularly suitable for the purposes of the present invention as they allow a precise size selective binding that is determined by the pH value that is used during binding. As is shown by the examples, even small variations in the pH value of the binding buffer/binding mixture have a significant influence on the cut-off value. This allows a precise adjustment of the desired cut-off value. Preferably, the guanidinium salt is selected from guanidinium hydrochloride and guanidinium (iso)thiocyanate. As is shown by the examples, guanidinium (iso)thiocyanate is particularly suitable for pH dependent size selection. The pH dependent size selective binding behaviour is used in the present invention in order to bind DNA molecules according to their size by varying the pH value during binding, respectively by adjusting the pH value to the desired cut-off size.

During binding, the chaotropic salt must be present in a sufficient concentration in order to promote adsorption of the DNA to the silicon containing surface of the binding matrix. Preferably, the binding buffer and/or the binding mixture comprises the chaotropic salt in a concentration that lies in a range selected from about 0.25M up to the saturation limit, about 0.4M to 7M, 0.5M to 6M, about 0.75M to 5.75M, 1M to 5.5M, 1.25M to 5M, 1.5M to 4.75M, 1.75M to 4.5M, 2M to 4.25M, 2.25M to 4M, 2.5M to 3.75M and 2.75M to 3.5M. If a chaotropic salt comprising one chaotropic ion is used, the concentration of the chaotropic ion corresponds to the concentration of the chaotropic salt. If a chaotropic salt is used which comprises a chaotropic anion and a chaotropic cation, the concentration of the chaotropic ions in the binding buffer, respectively the binding mixture is twice as high as the concentration of the chaotropic salt. The binding mixture comprises the chaotropic salt in a concentration wherein it is effective to induce, respectively promote binding of the DNA of the desired length to the silicon containing surface of the binding matrix. Higher concentrations of chaotropic salts promote binding. According to one embodiment, the chaotropic salt is present in the binding mixture and/or in the binding buffer in a concentration selected from $\geq 0.5M$, $\geq 0.75M$, $\geq 1M$, $\geq 1.25M$, $\geq 1.5M$, $\geq 1.75M$, $\geq 2M$, $\geq 2.25M$, $\geq 2.5M$, $\geq 2.75M$, $\geq 3M$, $\geq 3.25M$ and $\geq 3.5M$, preferably selected from $\geq 2.5M$, $\geq 2.75M$, $\geq 3M$, $\geq 3.25M$ and $\geq 3.5M$. As described above, the chaotropic salt preferably is a guanidinium salt such as guanidinium thiocyanate. Furthermore, guanidinium hydrochloride can be used as guanidinium salt as is demonstrated by the examples. Furthermore, a calcium salt such as $CaCl_2$ can be used. As is demonstrated by the examples, such calcium salt shows compared to guanidinium salts such as GuHCL a reverse pH dependency, in that an increase in the pH value lowers the cut-off value.

Furthermore, the binding buffer comprises a buffering agent. The buffering agent is important to maintain the pH value at the desired binding pH value and accordingly, to ensure that the desired cut-off value is achieved. As described herein, it was found that when using the binding conditions of the present invention, already small changes in the pH value may have a significant influence on the cut-off value and hence on the size of the recovered DNA molecules. Therefore, it is important that the pH value of the binding buffer, which also determines the pH value of the binding mixture, is sufficiently stable to reliably provide the desired binding pH and hence provides the desired cut-off value, thereby ensuring a reliable size selection. Therefore, a buffering agent is used which is suitable for buffering at the desired binding pH value. Suitable buffering agents are well-known in the prior art and include but are not limited to MOPS, TRIS, BIS-TRIS, BICINE, TRICINE, HEPES, organic acids such as carboxylic acids or their salts such as e.g. citrates and acetates, amino acids such as arginine and others. The buffering agent is chosen such that it has a buffering capacity that includes the desired binding pH value. As a rough estimate, a useful buffering capacity of a buffering agent is often pKa±1. E.g. a buffering agent suitable for buffering in a pH range of 10 to 11.5 is arginine.

Furthermore, not only the buffering capacity of the buffering agent is an important characteristic, but also its temperature dependency. E.g. many commonly used buffering agents such as TRIS have a temperature dependent pKa value. I.e. the pH value and buffering capacity changes depending on the temperature. Such behaviour can be disadvantageous for the purposes of the present invention, if a prepared binding buffer (e.g. provided in the form of a kit) is used, as small changes in the pH value of the binding buffer may already significantly influence the cut-off value and thus the lower size limit of the DNA molecules that are recovered. If the pH value of the binding buffer was adjusted at one temperature and the binding buffer is later on used at a significantly different (e.g. higher) temperature, this might influence the pH value of the binding buffer and hence the pH value of the binding mixture if no temperature stable buffering agent is used in the binding buffer. Therefore, to provide a binding buffer that is suitable for a kit format and that also reliably functions at different working temperatures, it is preferred to use a buffering agent which has a substantially temperature stable pKa. According to one embodiment, the buffering agent has a dpKa/dT value which is at most $-0.025/°$ C., at most $-0.020/°$ C., at most $-0.018/°$ C., at most $-0.017/°$ C., at most $-0.016/°$ C., at most $-0.015/°$ C., at most $-0.014/°$ C., at most $-0.013/°$ C., at most $-0.012/°$ C., at most $-0.011/°$ C. or which is at most at most $-0.01/°$ C. Suitable examples of temperature stable buffering agents include but are not limited to MOPS, PIPES, MOPSO, BES, HEPES, DIPSO, HEPPSO, POPSO, HEPPS, phosphate containing buffering agents or organic acid, in particular carboxylic acid based buffering agents such as e.g. acetates or citrates. Preferably, MOPS is used as buffering agent. As is demonstrated by the examples, a binding buffer comprising MOPS as buffering agent is stable and provides reliable size selection results. These results are also achieved at different temperatures. The achieved cut-off value can be easily adjusted by simple variation of the pH value of the binding buffer.

According to one embodiment, the binding buffer comprises the buffering agent in a concentration selected from 25 mM to 1M, 50 mM to 750 mM, 75 mM to 500 mM, 100 mM to 450 mM, 115 mM to 400 mM, 130 mM to 375 mM, 140 mM to 350 mM, 150 mM to 325 mM, 160 mM to 300 mM, 170 mM to 275 mM, 180 mM to 250 mM and 190 mM to 225 mM. As described above, preferably a buffering agent having a temperature stable pKa such as MOPs is used. It is preferred to use higher concentrations of buffering agent in the binding buffer, preferably of 100 mM or more, more preferred 125 mM or more or 150 mM or more. This ensures a reliable buffering capacity even if larger amounts of sample are added and avoids changes in the pH value in the binding mixture that is created when the sample is contacted with the binding buffer. As the binding pH value determines the cut-off value in the method according to the present invention, it is important to ensure that the desired binding pH value is obtained, respectively is maintained in the binding mixture after contacting the sample with the binding buffer.

The average length of the DNA molecules that bind to the binding matrix under the chosen binding conditions lies above the cut-off value while the average length of the DNA molecules which are not bound to the binding matrix lies below the cut-off value. The expression that "DNA molecules having a size above the cut-off value bind to the binding matrix" and similar expressions used herein, in particular specify that DNA molecules having a size at the cut-off value or above bind to the binding matrix. I.e. if the cut-off value is described as being 150 nt, this means that DNA molecules having a size of 150 nt or larger bind to the binding matrix. Thus, the cut-off value in particular defines the size of the DNA molecules that do not bind under the respective binding conditions, respectively the binding pH value to the binding matrix. According to one embodiment, the cut-off value refers to the length of the shortest DNA fragment that can be visualized by electropherogram. According to one embodiment, the cut-off value corresponds to the point where the curve of the electropherogram meets the x-axis. It is pointed out though that at this point, respectively the cut-off value, there usually is no quantitative recovery of the DNA but the percentage of captured DNA molecules increases with increasing size of the DNA molecules.

The binding pH value is chosen such that a cut-off value is obtained that allows to remove undesired small DNA molecules such as e.g. adaptors, adaptor-adaptor ligation products and primers. In the method according to the invention, DNA molecules having a size above the cut-off value are efficiently bound to the binding matrix in the presence of the chaotropic salt and hence are recovered during size selection. The precise cut-off value to be chosen and hence the appropriate binding pH value depends e.g. on the intended use of the DNA molecules and also the size of contaminating small DNA molecules that are not supposed to be bound and thus recovered during size selection. The removal of small DNA molecules that is achieved with the present invention does not necessarily be complete. For several applications it is sufficient that unwanted small DNA molecules are depleted to an extent that they do not significantly disturb or hamper the intended downstream reaction. As described, however, it is often not necessary that 100% is removed.

According to one embodiment, a binding pH value is used which sets the cut-off value in a range selected from 50 nt-1000 nt, 75 nt to 850 nt or 85 nt to 800 nt. According to one embodiment, a binding pH value is used which sets the cut-off value in a range selected from 100 nt to 750 nt, 100 nt to 700 nt, 100 nt to 600 nt, 110 nt to 500 nt, 110 nt to 450 nt, 100 nt to 400 nt, 110 nt to 375 nt, 115 nt to 350 nt, 120 nt to 325 nt, 125 nt to 300 nt, 125 nt to 275 nt, 125 nt to 250 nt, 130 nt to 225 nt, 130 nt to 200 nt, 135 nt to 190 nt, 135 nt to 180 nt, 140 nt to 170 nt and 145 nt to 160 nt. The sizes, respectively cut-off values indicated herein with reference to nucleotides "nt", refer to the chain length of the DNA molecules and thus are used in order to describe the length of, respectively describe the cut-off value for single-stranded as well as double-stranded DNA molecules. In double-stranded DNA molecules said nucleotides are paired. Hence, if the DNA is a double stranded molecule, what is preferred, the above indications with respect to the size or length in "nt" refers to "bp". Thus, if a double-stranded DNA molecule has a chain length, respectively size of 100 nt, said double-stranded DNA molecule has a size of 100 bp. The same applies to the definition of the cut-off value for double-stranded DNA molecules.

A cut-off value that lies in the range of 125 nt to 175 nt, preferably 135 nt to 170 nt such as e.g. of approx. 150 nt is e.g. particularly suitable for size selection during the preparation of a sequencing library. Here, size selection is in particular performed in order to separate adapter ligated DNA molecules from unligated adapter monomers and adapter-adapter ligation products, such as adapter dimers. The size of adapters that are commonly used for preparing sequencing libraries for next generation sequencing often lies in the range of 25 nt to 75 nt, in particular 30 nt to 60 nt. For removing unligated adapter monomers and adapter-adapter ligation products (such as in particular adapter dimers), the cut-off value is chosen such that it lies above the size of the adapter monomer(s) and above the size of the expected adapter-adapter ligation product(s). Preferably, the cut-off value is at least 10 nt, preferably at least 15 nt, at least 20 nt, at least 25 nt or at least 30 nt larger than the expected size of adapter-adapter ligation product(s) in order to ensure an efficient removal of the adapter monomer(s) and adapter-adapter ligation product(s).

In step a), DNA molecules having a size above the desired cut-off value (which is determined by the pH value) adsorb to the binding matrix which provides a silicon containing surface, preferably a siliceous surface for DNA binding. According to one embodiment, at least 80%, preferably at least 85%, more preferred at least 90%, more preferred at least 95%, more preferred at least 97%, at least 98%, at least 99% or at least 100% of the DNA molecules having a size above the cut-off value bind in step a). According to one embodiment, not more than 20%, not more than 15%, not more than 10%, not more than 7%, not more than 5%, not more than 4%, not more than 3%, not more than 2% or not more than 1%, of the DNA molecules having a size below the cut-off value bind to the binding matrix in step a).

As described above, the higher the binding pH-value, the higher the cut-off value and accordingly, the greater the lower size limit of the bound and thus recovered DNA molecules. This pH dependent effect is e.g. observed with a guanidinium salt as while other chaotropic salts such as $CaCl_2$ show an opposite pH dependent effect. According to one embodiment, the pH value of the binding buffer and/or the pH value of the binding mixture lies in a range selected from 7 to 11.25, 7.1 to 11.0, 7.2 to 10.75, 7.3 to 10.5, 7.4 to 10.25, 7.5 to 10.0, 7.6 to 9.8, 7.7 to 9.6, 7.8 to 9.5, 7.8 to 9.4, 7.8 to 9.3, 7.8 to 9.2, 7.8 to 9.1, 7.8 to 9.0, 7.8 to 8.9, 7.8 to 8.8, 7.8 to 8.7, 7.9 to 8.6, 7.9 to 8.5, 7.9 to 8.4, 7.9 to 8.3 and 8.0 to 8.2. The pH value is chosen such that the DNA molecules having the desired size are efficiently captured. Preferably, the binding buffer has a pH value ≥7, ≥7.3, ≥7.4, preferably ≥7.5, more preferred ≥7.6, most preferred ≥7.7. According to one embodiment, such pH value is also achieved in the binding mixture when the sample is contacted with the binding buffer. According to one embodiment, the pH value of the binding buffer and/or the binding mixture lies in a range of 7 to 9.5, preferably 7.1 to 9.4, 7.2 to 9.3, 7.3 to 9.2, 7.4 to 9.1, 7.5 to 9.0, 7.6 to 8.9, 7.7 to 8.8, 7.8 to 8.7 and 7.9 to 8.6. Exemplary embodiments of binding pH values that can be provided by the binding buffer and hence can be used as binding pH in the binding mixture, are also described subsequently. Due to the different pH values of said binding buffers, said binding buffers achieve when comprising the same type of chaotropic salt in the same concentration, different cut-off values. Thus, the subsequently described binding buffers may also be comprised in a set of binding buffers from which the user may chose the appropriate binding buffer that establishes the pH value in the binding mixture that provides the desired cut-off value.

Preferably, the subsequently described binding buffers comprise a guanidinium salt, preferably guanidinium(iso)thiocyanate. Preferably, said guanidinium salt is comprised in the binding buffer in a concentration of ≥2.5M, ≥2.75M, preferably, ≥3M, more preferably ≥3.25M or ≥3.5M. The binding buffer comprises a buffering agent which has an appropriate buffering capacity at the pH value of the binding buffer, preferably at least +/−0.2, at least +/−0.3, at least +/−0.4, at least +/−0.5, more preferred at least +/−0.75, most preferred at least +/−1 pH units. As described, the pH value of the binding buffer and/or the binding mixture can be established by using appropriate pH modifying substances such as acids or bases.

According to one embodiment, the binding buffer has a pH value that lies in the range of 7.9 to 8.2, preferably 8.0 to 8.1. When mixing said binding buffer with the DNA containing sample, a binding mixture is provided which has a binding pH value that also lies in the range of 7.9 to 8.2, preferably 8.0 to 8.1. As is demonstrated by Example 1, such a binding buffer is particularly suitable for size selection when using guanidinium thiocyanate.

According to one embodiment, the binding buffer has a pH value that lies in the range of 7.6 to 7.8, preferably 7.7 to 7.8. When mixing said binding buffer with the DNA containing sample, a binding mixture is provided which has a pH value that also lies in the range of 7.6 to 7.8, preferably 7.7 to 7.8. As is demonstrated by Example 1, such a binding buffer is particularly suitable for size selection when using guanidinium thiocyanate.

According to one embodiment the binding buffer has a pH value that lies in the range of 8.2 to 8.5, preferably 8.3 to 8.4. When mixing said binding buffer with the DNA containing sample, a binding mixture is provided which has a binding pH value that also lies in the range of 8.2 to 8.5, preferably 8.3 to 8.4.

According to one embodiment the binding buffer has a pH value that lies in the range of 8.5 to 8.8, preferably 8.6 to 8.7. When mixing said binding buffer with the DNA containing sample, a binding mixture is provided which has a binding pH value that also lies in the range of 8.5 to 8.8, preferably 8.6 to 8.7.

According to one embodiment the binding buffer has a pH value that lies in the range of 8.8 to 9.2, preferably 8.9 to 9.1. When mixing said binding buffer with the DNA containing sample, a binding mixture is provided which has a binding pH value that also lies in the range of 8.8 to 9.2, preferably 8.9 to 9.1.

According to one embodiment the binding buffer has a pH value that lies in the range of 9.2 to 9.5, preferably 9.3 to 9.4. When mixing said binding buffer with the DNA containing sample, a binding mixture is provided which has a binding pH value that also lies in the range of 9.2 to 9.5, preferably 9.3 to 9.4.

According to one embodiment the binding buffer has a pH value that lies in the range of 9.5 to 10.0, preferably 9.6 to 9.8. When mixing said binding buffer with the DNA containing sample, a binding mixture is provided which has a binding pH value that also lies in the range of 9.5 to 10.0, preferably 9.6 to 9.8.

According to one embodiment the binding buffer has a pH value that lies in the range of 10.0 to 10.5, preferably 10.1 to 10.3. When mixing said binding buffer with the DNA containing sample, a binding mixture is provided which has a binding pH value that also lies in the range of 10.0 to 10.5, preferably 10.1 to 10.3.

According to one embodiment the binding buffer has a pH value that lies in the range of 10.5 to 10.8, preferably 10.6 to 10.7. When mixing said binding buffer with the DNA containing sample, a binding mixture is provided which has a binding pH value that also lies in the range of 10.5 to 10.8, preferably 10.6 to 10.7.

According to one embodiment the binding buffer has a pH value that lies in the range of 10.8 to 11.25, preferably 10.8 to 11.0. When mixing said binding buffer with the DNA containing sample, a binding mixture is provided which has a binding pH value that also lies in the range of 10.8 to 11.25, preferably 10.8 to 11.0.

As described above, one or more of the above described binding buffers having a different pH value may be comprised in a binding buffer set. From said set the user may conveniently choose the binding buffer which achieves the desired cut-off value.

According to a preferred embodiment, the binding buffer comprises a guanidinium salt and a buffering agent which has a temperature stable pKa, preferably MOPS. Preferably, said binding buffer has a pH value ≥7, preferably ≥7.5, more preferred ≥7.6, most preferred ≥7.7. MOPS has a good buffering capacity in the pH range of 6.2 to 8.2. According to one embodiment, the pH value of the binding buffer lies in said range, preferably in a range of 7.5 to 8.2, preferably 7.7 to 8.1 and preferably, such pH value is also achieved in the binding mixture when the sample is contacted with the binding buffer. According to one embodiment, the binding buffer is an aqueous solution which comprises and preferably consists of a guanidinium salt in a concentration selected from the range of 1.5M-5M, preferably 2M to 4.5M, more preferred 2.5M to 4M, most preferred 3M to 3.75M; and a temperature stable buffering agent in a concentration selected from the range 100 mM to 500 mM, preferably 125 mM to 400 mM, more preferred 150 mM to 300 mM, more preferred 175 mM to 250 mM.

Preferably, said binding buffer does not comprise any additional ingredients. Preferably, GTC is used as guanidinium salt and MOPS is used as temperature stable buffering agent. According to one embodiment, said binding buffer has a pH value that lies in the range of 7.9 to 8.2, preferably 8.0 to 8.1. When mixing said binding buffer with the DNA containing sample, a binding mixture is provided which has a binding pH value that also lies in the range of 7.9 to 8.2, preferably 8.0 to 8.1. The cut-off value lies in this embodiment in the range of 125 nt to 170 nt, in particular 135 nt to 160 nt, preferably at approx. 150 nt. According to one embodiment, said binding buffer has a pH value that lies in the range of 7.6 to 7.8, preferably 7.7 to 7.8. When mixing said binding buffer with the DNA containing sample, a binding mixture is provided which has a pH value that also lies in the range of 7.6 to 7.8, preferably 7.7 to 7.8. The cut-off value lies in this embodiment in the range of 80 nt to 120 nt, in particular 90 nt to 110 t and in particular at approx. 100 nt. Preferably, the binding buffer has a composition as described in the penultimate paragraphs.

According to one embodiment, a calcium salt is used as chaotropic salt. As is demonstrated by the examples, $CaCl_2$ shows a similar pH dependent binding effect as GuHCl, wherein, however, $CaCl_2$ selected the DNA in opposite orientation. The higher the pH value during binding, the lower was the cut-off value. A size selective effect was in particular seen at a pH value that lies in the range of 7 to 8. Therefore, according to one embodiment, the pH value is selected from the range of 7 to 8, depending on the desired cut-off value. $CaCl_2$ may be contained in a concentration of at least 2M, preferably at least 2.25M. Suitable buffering agents were described above, MOPS being preferred for the above described reasons. According to one embodiment, MOPS is used in a concentration selected from the range of 50 mM to 200 mM, preferably 75 mM to 150 mM.

The binding matrix comprises a silicon containing surface to which the DNA having a size above the cut-off value binds under the chosen binding conditions. Binding is in particular achieved by adsorption. Preferably, the binding matrix provides a silica surface. The term "silica surface" as used herein includes surfaces comprising or consisting of silicon dioxide and/or other silicon oxides, diatomaceous earth, glass, zeolithe, bentonite, alkylsilica, aluminum silicate and borosilicate. The binding matrix has an unmodified silicon containing surface. In particular, the binding matrix provides an unmodified silica surface. Therefore, the surface is not modified with nucleic acid binding ligands or other nucleic acid binding groups. E.g., the binding matrix does not carry any ligands at its binding surface that comprise ion exchange groups, in particular, the surface of the binding matrix is not modified with functional ligands. In particular, it is not modified with ligands comprising anionic or cationic exchange groups such as e.g. amine groups or carboxyl groups. The method according to the present invention is based on the adsorption of the DNA to the silicon containing surface of the binding matrix in the presence of a chaotropic salt. The method according to the present invention is not based on ion exchange which involves the use of ion exchange groups at the surface of the binding matrix. Preferably, the surface of the binding matrix does not comprise, respectively does not carry, any ligands. According to one embodiment, the silica surface does not comprise any functional groups besides its silanol groups or other oxidized forms of silicon, like oxides. Exemplary binding matrixes that can be used in conjunction with the present invention include, but are not limited to, binding matrixes comprising a silica surface, including but not limited to, silica particles, silica fibres, glass materials such as e.g. glass powder, glass fibres, glass particles or controlled pore glass, silicon dioxide, glass or silica in particulate form such as powder, beads or frits. The term binding matrix is not intended to imply any limitation regarding its form or design. Thus, the term binding matrix encompasses appropriate materials having a silicon containing surface, in particular a silica surface that is porous or non-porous; permeable or impermeable; Suitable binding matrices include but are not limited to membranes, filters, sheets, particles, magnetic particles, beads, gels, powders, fibres and the like. Particularly preferred is the use of silicon containing materials such as silica and polysilicic acid materials, borosilicates, silicates and anorganic glasses as binding matrix. The binding matrix comprising an unmodified silica surface may e.g. have the form of a filter, fibres, membrane or particles. According to the present invention, the use of a column based binding matrix or the use of particles, in particular magnetic particles, is preferred.

According to one embodiment, silica particles are used that may have the form of beads. Preferably, said particles have a size of about 0.02 to 30 µm, more preferred 0.05 to 15 µm and most preferred of 0.1 to 10 µm. To ease the processing of the nucleic acid binding solid phase, preferably magnetic silica particles are used. Magnetic particles respond to a magnetic field. The magnetic silica particles may e.g. be ferrimagnetic, ferromagnetic, paramagnetic or superparamagnetic. Suitable magnetic silica particles are for example described in WO 01/71732, WO 2004/003231 and WO 2003/004150. Other magnetic silica particles are also known from the prior art and are e.g. described in WO 98/31840, WO 98/31461, EP 1 260 595, WO 96/41811 and EP 0 343 934 and also include for example magnetic silica glass particles. The use of magnetic particles has advantages, because the magnetic particles including the bound DNA can be processed easily by the aid of a magnetic field, e.g. by using a permanent magnet. This embodiment is e.g. compatible with established robotic systems capable of processing magnetic particles. Here, different robotic systems exist in the prior art that can be used in conjunction with the present invention to process the magnetic silica particles to which the DNA was bound. According to one embodiment, magnetic particles are collected at the bottom or the side of a reaction vessel and the remaining liquid sample is removed from the reaction vessel, leaving behind the collected magnetic particles to which the DNA molecules are bound. Removal of the remaining sample can occur by decantation or aspiration. Such systems are well known in the prior art and thus need no detailed description here. In an alternative system that is known for processing magnetic particles the magnet which is usually covered by a cover or envelope plunges into the reaction vessel to collect the magnetic particles. As respective systems are well-known in the prior art and are also commercially available (e.g. QIASYMPHONY®; QIAGEN), they do not need any detailed description here. In a further alternative system that is known for processing magnetic particles, the sample comprising the magnetic silica particles can be aspirated into a pipette tip and the magnetic particles can be collected in the pipette tip by applying a magnet e.g. to the side of the pipette tip. The remaining sample can then be released from the pipette tip while the collected magnet silica particles which carry the bound DNA remain due to the magnet in the pipette tip. The collected magnetic particles can then be processed further. Such systems are also well-known in the prior art and are also commercially available (e.g. BioRobot EZ1, QIAGEN) and thus, do not need any detailed description here.

According to one embodiment, the binding matrix is comprised in a column. The term "column" as used herein in particular describes a container having at least two openings. Thereby, a solution and/or sample can pass through said column. The term "column" in particular does not imply any restrictions with respect to the shape of the container which can be e.g. round or angular and preferably is cylindrical. However, also other shapes can be used, in particular when using multi-columns. The column comprises the binding matrix that is used for DNA binding. Said binding matrix comprised in the column should allow the passage of a solution, respectively the binding mixture when applied to the column. This means that if e.g. a centrifuge force is applied to the column, a solution and/or the binding mixture is enabled to pass through the column in direction of the centrifuge force. As discussed above, when using a respective column based DNA isolation procedure, the binding mixture is usually passed through the column, e.g. assisted by centrifugation or vacuum, and the DNA molecules having a size above the cut-off value bind to the comprised binding matrix during said passage. The column can be used in a single format or in a multi-format. Such multi-columns having a similar format as multi-well plates and which comprise a binding matrix such as a silica membrane or glass fibres, are well-known in the prior art and are also commercially available. Preferably, the column is a spin column. Preferably, a DNA binding membrane or DNA binding fibres are used as binding matrix. Examples include but are not limited to silica membranes, glass fibre membranes or filters providing a silicon containing surface for DNA binding. Preferably, the membrane is porous. As is shown by the examples, using a binding matrix comprised in a column has several advantages. The use of columns such as spin columns is widely established for DNA purification, and thus, the use of columns is very convenient for the user. Column based methods are also fast and, furthermore, automated systems exist that allow the automated processing of the samples (see e.g. QIAcube, QIAGEN). Thereby, tedious manual handling procedures can be avoided. Furthermore, using a spin column based approach for size selectively isolating DNA has the advantage that there is no risk of carryover of potentially inhibitory components from the washing solutions (such as e.g. alcohol) or beads. It is preferred to use a membrane or fibres as binding matrix which comprise or consist of silica in the column. As is shown in the examples, respective column materials are particularly suitable for precisely adjusting the cut-off value within a narrow range. The cut-off value can be adjusted more precisely. Suitable and preferred silica based materials which provide a silica surface suitable for DNA binding were also described above. A further common binding matrix comprised in a column is a fill of silica particles, or a layer of a silica material (e.g. a silica gel). E.g. the silica particles can be arranged as a layer on an inert filter or membrane, thereby forming a DNA binding matrix. To alleviate the passage of the binding mixture through the binding matrix comprised in the column, suitable means can be used such as e.g. centrifugation or the use of a pressure difference-generating apparatus which e.g. presses the sample through the column, respectively the binding matrix or sucks it through the binding matrix by applying a vacuum. Respective means are well known in the prior art and thus need no further description here.

As described above, the chaotropic salt promotes binding of the DNA to the surface of the binding matrix, wherein the pH value established during binding determines the cut-off value and thus, determines the size of the DNA molecules that are bound and hence recovered during size selection. The higher the pH value, the higher the cut-off value, i.e. the longer the length of DNA molecules that can efficiently adsorb to the surface of the binding matrix. This pattern is e.g. observed for chaotropic salts such as guanidinium salts. For other chaotropic salts such as $CaCl_2$, an opposite pH dependency is observed. Here, the higher the pH value, the lower is the cut-off value as is demonstrated by the examples. DNA molecules having a size shorter than the cut-off value cannot bind and thus, are removed during the size selective purification process. Thus, by varying the pH value, the cut-off value can be precisely determined, thereby allowing a precise size selective DNA isolation. That a change in the pH value of the binding buffer, respectively the binding mixture, allows a precise size selection of DNA molecules, even if the type and substantially also the concentration of the chaotropic salt remains the same was very surprising.

The method according to the present invention does not involve the use of phenol, phenol/chloroform and/or chloroform. Preferably, no organic solvents such as e.g. alcohols are added, respectively are present in step a) during DNA binding. According to one embodiment, binding is performed in the absence of additional binding enhancers, in particular in the absence of binding enhancers selected from the group consisting of alcohols, polymers such as PEG, detergents and additional salts besides the chaotropic salt that is used for binding. Therefore, according to one embodiment, no such binding enhancers are comprised in the binding buffer. According to one embodiment, the DNA containing sample is not a lysate. According to one embodiment, no additional agents are added to the DNA containing sample to prepare the binding mixture except for the binding buffer. As described above, preferably, the binding buffer is an aqueous solution which consists of the chaotropic salt(s) and the buffering agent(s).

Contacting the DNA containing sample with the binding buffer to provide the binding mixture and binding of the DNA molecules to the binding matrix may be performed simultaneously or sequentially. According to one embodiment, the DNA containing sample is contacted with the binding buffer and the resulting binding mixture is then contacted with the binding matrix. This embodiment is e.g. feasible if a column-based isolation protocol is used. A likewise approach can also be used when using a particulate binding matrix such as e.g. magnetic silica particles. When using a particulate binding matrix, the binding matrix, the binding buffer and the sample can be added in any order. E.g. it is within the scope of the present invention to first provide the binding matrix and the binding buffer and then add the sample or to first provide the sample, the binding matrix and then add the binding buffer. Preferably, the binding buffer is mixed with the sample to provide the binding mixture.

At the end of step a), the DNA molecules having a size above the cut-off value are bound to the binding matrix.

Step b)

In step b), the DNA that is bound to the binding matrix is separated from the remaining sample. Thereby, the adsorbed DNA having a size above the cut-off value is separated from unbound DNA molecules and optionally other contaminants and impurities present in the sample. Suitable separation methods are well known in the prior art and the appropriate separation technique also depends on the used binding matrix. E.g. when using a column based approach, separation is usually achieved when the binding mixture passes through the column. The DNA binds to the binding matrix comprised in the column while the remaining sample passes through the column and thereby is separated from the bound DNA. As described above, this process can be assisted e.g. by centrifugation or by applying a vacuum. When using a particulate binding matrix such as e.g. silica particles, the particles can be collected by sedimentation which can be assisted by centrifugation or magnetic separation if magnetic particles are used. Suitable embodiments were described above in conjunction with the different formats of the binding matrix and are also well-known to the skilled person.

Step c)

In optional step c), the bound DNA is washed. Here, one or more washing steps can be performed. Even though this step is optional, it is preferably performed in order to efficiently remove unbound components and impurities such as e.g. nucleotides and enzymes from previous reactions. This is particularly suitable if the DNA containing sample was obtained during the preparation of a sequencing library. Furthermore, washing steps are also suitable remove traces of the chaotropic salt used during binding, if it could interfere with the intended downstream process.

Thus, according to a preferred embodiment, one or more washing steps are performed in step c) in order to further purify the bound DNA molecules. For this purpose, common washing solutions may be used. A suitable washing solution removes impurities but not the DNA that is bound to the binding matrix.

According to one embodiment, the solution used for washing comprises at least one chaotropic salt and/or at least one alcohol. Chaotropic salts that can be used in the washing solutions include but are not limited to guanidinium hydrochloride, guanidinium thiocyanate, guanidinium isothiocyanate and sodium iodide or other chaotropic salts (see also above). As alcohol, short chained branched or unbranched alcohols with preferably one to 5 carbon atoms can be used for washing, respectively can be used in the washing solution. Also mixtures of alcohols can be used. Suitable alcohols include but are not limited to methanol, ethanol, propanol, isopropanol and butanol. Preferably, isopropanol and/or ethanol are used in the washing solution.

A further suitable washing solution which can be used alternatively or also in addition to the washing solutions described above comprises an alcohol and a buffering agent. Suitable alcohols and buffering agents such as biological buffers are described above. Preferably, isopropanol or ethanol, most preferred ethanol is used for this second washing step. Preferably, ethanol is used in a concentration of at least 60% (v/v), at least 70% (v/v), preferably at least 80% (v/v). The buffering agent may preferably be Tris e.g. at a pH of approx. 7 to 8.

A further suitable washing solution which can be used alternatively or optionally also in addition to the washing solutions described above comprises an alcohol but no salt. This allows to wash away salts. Preferably, isopropanol or ethanol, most preferred ethanol is used for washing. Preferably, the alcohol is comprised in a concentration of at least 50% v/v, at least 60% v/v, preferably at least 70% v/v. Preferably, the concentration lies in a range of 50% v/v to 100% v/v, more preferred 70% v/v to 100% v/v.

Residual alcohol that may be present after the washing step in case an alcohol containing washing solution was used can be removed e.g. by air drying (e.g. suitable when working with a particulate binding matrix) or by an additional centrifugation step if using a column based binding matrix. Respective methods and procedures are well-known in the prior art and thus, do not need any further description here.

Step d)

In optional step d), one or more elution steps are performed in order to elute the purified size selected DNA. However, the bound DNA may also be processed while being bound to the binding matrix, depending on the intended downstream application, respectively the intended use of the DNA. E.g. a particulate binding matrix such as magnetic particles may be directly subjected to an amplification reaction without prior separate elution of the bound DNA.

However, it is preferred to elute the DNA. Here, basically any elution solution can be used which effects desorption of the bound DNA from the binding matrix. Classical elution solutions known to effectively elute DNA from a silica surface include but are not limited to water, elution buffers such as TE-buffer and low-salt solutions which have a salt content of 150 mM or less, preferably 100 mM or less, more preferred 75 mM or less, 50 mM or less, 25 mM or less, 20 mM or less, 15 mM or less, 10 mM or less or are salt-free. The elution solution may e.g. comprise a buffering agent, in particular may comprise a biological buffer such as Tris, MOPS, HEPES, MES, BIS-TRIS, propane and others. The buffering agent may be present in a concentration of 150 mM or less, preferably 100 mM or less, more preferred 75 mM or less, 50 mM or less, 25 mM or less, 20 mM or less, 15 mM or less or 10 mM or less. According to one embodiment, the elution buffer has a pH value that is selected from pH 6.5 to pH 10, pH 7 to pH 9.5, pH 7.5 to 9.0, pH 7.75 to pH 8.75, pH 8 to pH 8.5. Elution can be assisted by heating and/or shaking what is e.g. particularly feasible if a particulate binding matrix is used. If a column based binding matrix is used, the elution buffer is usually applied to the column and forced through the binding matrix which can be assisted again e.g. by centrifugation or by applying pressure or a vacuum.

Preferably, an elution solution is used that does not interfere with the intended downstream application. Thus, according to one embodiment, the elution buffer does not comprise a complexing agent such as EDTA. EDTA, in particular in higher concentrations, may inhibit downstream reactions.

Furthermore, it is also within the scope of the present invention to repeat the elution step in order to ensure that the bound DNA is efficiently released from the binding matrix.

The method for isolating DNA by size according to the present invention is highly precise and reproducible with respect to the size of the isolated DNA molecules. Unexpectedly, this precise size selection could be achieved despite of the low complexity of the method. In particular, by using one size selective binding step at one particular binding pH, DNA molecules having a desired minimum size can be size selectively bound. Due to this straight-forward size selective binding step, the method according to the present invention is optimally suitable for batch procedures. This also distinguishes the methods of the present invention from prior art chromatographic methods which were used for size separation of nucleic acids, e.g. using titratable anion exchange compositions. The methods of the present invention in particular do not need highly specific and expensive apparatuses, do not need the generation and use of binding and/or elution buffer gradients and the collection and screening of multitudes of elution fractions. Therefore, according to one embodiment, no pH gradients are used in the method according to the present invention. In particular, no pH gradient is used to establish the binding pH value. Preferably, a single binding buffer having a specific, fixed pH value is contacted with the DNA containing sample to provide a binding mixture which has a specific, fixed binding pH value. Preferably, no pH variations such as e.g. manual pH adjustments, are performed during the binding step and the pH value that is established in the binding mixture by contacting the binding buffer with the sample is the binding pH that is used to achieve binding of the DNA molecules having a size above the cut-off value to the binding matrix.

Specific Embodiments

Non-limiting preferred embodiments and applications of the method according to the present invention will now be described in the following. As discussed above, the size selective DNA isolation method according to the present invention is in particular suitable for enriching DNA molecules having a desired length above a certain cut-off value from a mixed population of DNA molecules having different lengths. The method is in particular suitable for removing non-target DNA molecules which have a size below a certain cut-off value by binding and thus isolating target DNA molecules having a desired minimum size above the cut-off value from the DNA containing sample.

According to one embodiment, the method according to the present invention is performed more than once. Thus, according to one embodiment, at least two size selective DNA isolation cycles using the method of the present invention comprising steps a) to d) are performed. According to one embodiment, the eluate that is obtained in the first size selection cycle provides the DNA containing sample for the second size selection cycle. Thus, the eluate obtained after the first size selection cycle is contacted in the second size selection cycle in step a) with the binding buffer in order to provide a binding mixture and to bind DNA molecules having a size above the desired cut-off value to the binding matrix. According to one embodiment, the same binding buffer and the same binding pH value are used in the second size selection cycle as in the first size selection cycle. According to another embodiment, a binding buffer having the same composition but a different, e.g. lower, pH value is used in the second size selection cycle. Steps b) to d) are then again performed as described above. Preferably, the same binding matrix is used in the first and second size selection cycle. Preferably, a column based binding matrix is used. E.g. the binding mixture that is obtained in the second size selection cycle after contacting the eluate obtained after the first size selection cycle with the binding buffer can be reapplied to the column based binding matrix that was used in the first size selection cycle. Performing at least two size selection cycles according to the present invention is particularly favourable to remove large amounts of contaminating short DNA fragments such as e.g. adapter monomers or adapter-adapter ligation products during the preparation of a sequencing library, in particular a sequencing library suitable for next generation sequencing.

According to one embodiment, the method according to the present invention is used for fractionating DNA molecules comprised in a DNA containing sample according to their size. Thereby, two or more fractions are obtained, wherein the DNA molecules comprised in the different fractions differ on average in their length. The method according to the present invention is also suitable for said purpose. For fractionating a DNA containing sample, e.g. two or more size selective DNA isolation cycles comprising steps a) to d) of the method according to present invention are performed. Said steps a) to d), in particular suitable binding buffers and binding matrixes, were already described in detail above. It is referred to the above detailed disclosure. Size fractionation can be achieved as follows:

in the first size selective DNA isolation cycle A a binding pH value A is provided in the binding mixture which determines the cut-off value A, and wherein the obtained eluate A provides a fraction which predominantly comprises DNA molecules having a size above the cut-off value A;

wherein the separated remaining sample obtained in step b) of the first size selective DNA isolation cycle A provides the DNA containing sample for the second size selective DNA isolation cycle B, and wherein a binding pH value B is provided in the binding mixture which determines the cut-off value B, wherein the cut-off value B is smaller than the cut-off value A and wherein the obtained eluate B provides a fraction which predominantly comprises DNA molecules having a size above the cut-off value B but below the cut-off value A.

Therefore, in the first size selective DNA isolation cycle A, longer DNA molecules having a size that lies above the cut-off value A are isolated and thus provided in the eluate A. Thereby, a first fraction comprising DNA molecules predominantly having a size above the cut-off value A is provided. The remaining sample that was separated from the bound DNA comprises the shorter DNA molecules that have a size below the cut-off value A. Said remaining sample provides the DNA containing sample for the second size selective DNA isolation cycle B, wherein the remaining DNA molecules are again separated according to their size using the method of the present invention. Eluate B provides a second fraction comprising DNA molecules predominantly having a size above the cut-off value B, but below the cut-off value A.

According to one embodiment, the pH value of the binding buffer A that is used in the first size selective DNA isolation cycle A is higher than the pH value of the binding buffer B that is used in the second size selective DNA isolation cycle B. This embodiment is advantageous if adjustments of the pH value in the binding mixture are to be avoided and wherein the binding pH value is adjusted by the binding buffer and wherein the binding pH value preferably corresponds to the pH value of the binding buffer.

According to one embodiment, the binding buffers A and B comprise the same chaotropic salt in the same concentration, and preferably have the same composition, but a different pH value. Preferably, the pH value of binding buffer A is at least 0.2 pH units higher than the pH value of the binding buffer B. According to one embodiment, the pH value of binding buffer A is at least at least 0.3 pH units, at least 0.4 pH units, at least 0.5 pH units, at least 0.6 pH units, at least 0.7 pH units, at least 0.8 pH units, at least 0.9 pH units, at least 1.0 pH units, at least 1.1 pH units, at least 1.2 pH units, at least 1.3 pH units, at least 1.4 pH units or at least 1.5 pH units higher than the pH value of the binding buffer B. According to one embodiment, cut-off value A is at least 25 nt, at least 50 nt, at least 75 nt, at least 100 nt, at least 125 nt or at least 150 nt greater than cut-off value B.

If desired, the DNA molecules having a size smaller than the cut-off value B that are still comprised in the remaining sample can be subjected to a third size selective DNA isolation cycle C, if desired. Thus, according to one embodiment, a size selective DNA isolation cycle C is performed, wherein the separated remaining sample obtained in step b) of the second size selective DNA isolation cycle B provides the DNA containing sample for the third size selective DNA isolation cycle C, and wherein a binding pH value C is provided in the binding mixture which determines the cut-off value C, wherein the cut-off value C is smaller than the cut-off value B and wherein the obtained eluate C provides a fraction which predominantly comprises DNA molecules having a size above the cut-off value C but below the cut-off value B. The pH value of the binding buffer B that is used in the second size selective DNA isolation cycle B is according to one embodiment higher than the pH value of the binding buffer C that is used in the third size selective DNA isolation cycle C. According to one embodiment, the binding buffers A, B and C have the same composition but a different pH value. Preferably, the pH value of binding buffer B is at least 0.2 pH units higher than the pH value of the binding buffer C. According to one embodiment, the pH value of binding buffer B is at least at least 0.3 pH units, at least 0.4 pH units, at least 0.5 pH units, at least 0.6 pH units, at least 0.7 pH units, at least 0.8 pH units, at least 0.9 pH units, at least 1.0 pH units, at least 1.1 pH units, at least 1.2 pH units, at least 1.3 pH units, at least 1.4 pH units or at least 1.5 pH units higher than the pH value of the binding buffer C. According to one embodiment, the cut-off value B is at least 25 nt, at least 50 nt, at least 75 nt, at least 100 nt, at least 125 nt or at least 150 nt greater than the cut-off value C. Also further subsequent size selective DNA isolation cycles can be performed analogously if a further size fractionation of the remaining sample is desired.

Suitable binding buffers having different pH values and which accordingly establish a different cut-off value were also described above, e.g. also in conjunction with the embodiment wherein a set of binding buffers is used. According to one embodiment, a set of binding buffers is used, wherein for each size selective DNA isolation cycle a suitable binding buffer is provided that establishes a cut-off value suitable for the respective size selective DNA isolation cycle. Preferably, said set of binding buffers comprises at least a binding buffer A, a binding buffer B and optionally a binding buffer C.

A different size fractionation embodiment comprises performing a first size selective DNA isolation cycle A comprising steps a) to d) according to the method of the first aspect of the present invention, wherein a binding pH value A is provided in the binding mixture which determines the cut-off value A, and wherein the obtained eluate A provides a fraction which predominantly comprises DNA molecules having a size above the cut-off value A;

wherein the separated remaining sample obtained in step b) of the first size selective DNA isolation cycle A provides the binding mixture for a second size selective DNA isolation cycle B, wherein the pH value of the binding mixture is adjusted to a binding pH value B which determines the cut-off value B, wherein the cut-off value B is smaller than the cut-off value A and binding DNA molecules having a size above the cut-off value B to a binding matrix which has a silicon containing surface; separating the bound DNA from the remaining sample, washing the bound DNA; and eluting the bound DNA from the binding matrix, thereby providing an eluate B which provides a fraction which predominantly comprises DNA molecules having a size above the cut-off value B but below the cut-off value A.

This embodiment is based on a similar principle as the size fractionation method described above. However, in the second size selective DNA isolation cycle B, only the pH value of the remaining sample of the first size selective DNA isolation cycle A is adjusted, i.e. lowered to the binding pH value B, which provides the desired cut-off value B. As the remaining sample obtained in step b) of the first size selective DNA isolation cycle A after separating the binding matrix with the bound DNA basically corresponds to the binding mixture (from which the DNA molecules having a size above the cut-off value A were removed) which accordingly, comprises the chaotropic salt in an appropriate concentration for binding, the binding conditions for the second size selective DNA isolation cycle B can be adjusted by merely lowering the pH value of the binding mixture to the binding pH value B, which determines the cut-off value B. Further analogous size selective DNA isolation cycles can be performed subsequently if desired. As described above, according to one embodiment, cut-off value A is at least 25 nt, at least 50 nt, at least 75 nt, at least 100 nt, at least 125 nt or at least 150 nt greater than cut-off value B.

As discussed above, the method according to the present invention is in particular suitable for size selection in the context of next generation sequencing. The preparation of a sequencing library suitable for next generation sequencing usually is a multi-step process wherein at different stages of said process a size-selection of the provided DNA molecules can be performed. At which stage of said process a size selection is performed also depends on the library preparation method used. Suitable embodiments will be described in the following. The size selection method according to the present invention is in particular suitable for use in the context of preparing a sequencing library, as it allows the separation of DNA fragments with only small differences in size, e.g. as described herein, the removal of unwanted adapter dimers (approx. 120 bp) from the desired DNA fragments (150 bp and larger) in library construction protocols for next generation sequencing applications. The present invention allows the specific adjustment of a precise size-selective DNA binding by changing the binding pH value, while maintaining the type of chaotropic salt and concentration of chaotropic salt.

A sequencing library which is suitable for massive parallel sequencing and accordingly, is suitable for next generation sequencing can be prepared using methods known in the prior art. The preparation of a respective sequencing library often involves the generation of a plurality of double-stranded, linear DNA fragments from a nucleic acid containing sample. For example, DNA, such a genomic DNA or cDNA, can be fragmented for example by shearing, such as sonification, hydro-shearing, ultrasound, nebulization or enzymatic fragmentation, in order to provide DNA fragments that are suitable for subsequent sequencing. The length of the fragments can be chosen based on the sequencing capacity of the next generation sequencing platform that is subsequently used for sequencing. Usually, the obtained fragments have a length of 1500 bp or less, 1000 bp or less, 750 bp or less, 600 bp or less and preferably 500 bp or less as this corresponds to the sequencing capacity of most current next generation sequencing platforms. Preferably, the obtained fragments have a length that predominantly lies in a range of 50 bp to 1000 bp, more preferred 75 bp to 900 bp, 100 bp to 850 bp, 110 bp to 800 bp, 115 bp to 750 bp, 120 bp to 700 bp, 125 bp to 650 bp, 130 bp to 600 bp, 135 bp to 550 bp, 140 bp to 500 bp and 145 bp to 450 bp. Respective fragment sizes are particularly suitable for genomic DNA, also considering that the size of an exon is approx. 150 bp to 200 bp in length and respective short fragments can be efficiently sequenced using common next generation sequencing platforms. However, also longer fragments can be useful, e.g. if using next generation sequencing methods which allow longer sequence reads.

According to one embodiment, the fragmented DNA is repaired after fragmentation and end polished using methods known in the prior art, thereby providing DNA fragments having blunt ends. In such methods which are well-known in the prior art, overhangs resulting from the fragmentation process are converted into blunt ends. As the respective methods are well-known in the prior art, they do not need any detailed description herein.

According to one embodiment, the size selective DNA isolation method according to the invention is performed after DNA fragments were obtained, preferably after the fragmented DNA was end polished to provide DNA fragments having blunt ends. A size selective DNA isolation at this stage allows e.g. to eliminate very short DNA fragments which do not have the appropriate length for subsequent sequencing. As discussed above, the cut-off value for DNA binding can be adjusted by appropriate choice of the binding pH value.

According to one embodiment, after end-repair and optionally size selection, an overhang is added to the 3' ends of the blunt end fragments. Preferably, a single nucleotide overhang is added. E.g. a single "A" nucleotide can be added using methods well-known in the prior art. This is also referred to as "A tailing". A respective nucleotide overhang prevents the fragments from ligating to one another during the subsequent adapter ligation reaction. E.g. a corresponding single "T" or other complementary overhang can be provided at the 3' end of the adapters to provide a complementary overhang for ligating the adaptors to the DNA fragment. This ensures a low rate of chimera (concatenated template) formation. However, also other strategies are known in the prior art to ensure proper ligation of sequencing adapters. E.g. also blunt end adapters can be ligated.

According to a preferred embodiment, adapters are ligated to the 5' and/or 3' ends of the obtained DNA fragments, preferably at both ends of the DNA fragments. The specific design of the adapters depends on the next generation sequencing platform to be used and for the purposes of the present invention, basically any adaptors used for preparing sequencing libraries for next generation sequencing can be used. The adapter sequences provide a known sequence composition allowing e.g. subsequent library amplification and/or sequencing primer annealing. As adaptors, double-stranded or partially double-stranded nucleic acids of known sequence can be used. The adapters may have blunt ends, cohesive ends with 3' or 5' overhangs, may be provided by Y shaped adapters or by stem-loop shaped adapters. Y shaped adapters are e.g. described in U.S. Pat. No. 7,741,463 and stem-loop shaped adapters are e.g. described in US2009/0298075, herein incorporated by reference regarding the specific design of the adapters. Preferably, the adaptors have a length of at least 7, preferably at least 10, preferably at least 15 bases. The adapter length preferably lies in a range of 10 to 100 bases, preferably 15 to 75 bases, more preferred 20 to 60 bases. Either the same or different adapters can be used for the 3' and 5' end of the DNA fragments. Using the same type of adaptor for both ends, such as e.g. a Y shaped or a stem-looped shaped adapter, has the advantage that no fragments are lost during library preparation due to adapter mispairing which is an advantage when working with low amounts of DNA.

Thus, preferably, a sequencing library is prepared which comprises randomly fragmented double stranded DNA molecules which are ligated at their 3' and 5' end to adapter sequences. The adaptors provide a known sequence and thus provide a known template for amplification and/or sequencing primers. Optionally, the adapters may also provide an individual index thereby allowing the subsequent pooling of two or more target enriched sequencing libraries prior to sequencing. This embodiment will be described in further detail below.

To ensure an efficient adapter ligation, the adapters are usually used in excess during the adapter ligation step. Thus, after adapter ligation, a DNA containing sample is provided which comprises DNA molecules that are flanked by adapters in addition to unligated adapter monomers and adapter-adapter ligation products such as adapter dimers. As is shown by the examples (see in particular FIG. 5), unligated adapter monomers and adapter-adapter ligation products are usually comprised in large amounts in the sample that is obtained after the adapter ligation process. It is important to remove these unligated adapter monomers and adapter-adapter ligation products as they otherwise diminish the sequencing power of the subsequent sequencing reaction. To remove unligated adapter monomers and adapter-adapter ligation products as well as enzymes and other contaminants from the adapter ligation sample, it is preferred to perform a size selective DNA isolation using the method according to the present invention. The prior art usually uses a PEG/bead based method or a size selection process that is based on gel purification. These common prior art methods are more time consuming than the method according to the present invention and the size selective DNA isolation method according to the present invention also provides better results than the PEG/bead based prior art method as is demonstrated in the examples. Therefore, it is particularly preferred to perform a size selective DNA isolation according to the present invention after adapter ligation in a sequencing library preparation process, in order to remove unligated adapter monomers and adapter-adapter ligation products and other contaminants. The cut-off value for DNA binding that is determined by the pH value used during binding is chosen such that it lies above the size of unligated adapter monomers and above the size of expected adapter-adapter ligation products. This ensures that unligated adapter monomers and adapter-adapter ligation products are not captured during said size selective DNA isolation step and thus are depleted from the isolated DNA, which predominantly comprises DNA molecules having a size above the cut-off value. The method according to the present invention is particularly advantageous for this purpose, because the cut-off value can be precisely adjusted within a narrow range by appropriate choice of the pH value of the binding buffer. No complicated adjustments or modifications of the binding conditions are necessary. Therefore, the method of the present invention is fast and convenient to perform.

According to one embodiment, DNA fragments are enriched after adapter ligation (and preferably size selection as described above) using amplification, preferably PCR amplification. Such enrichment step is optional, but preferred for some applications. E.g. an amplification reaction such as a PCR amplification can be used to selectively enrich those DNA fragments that have adapter molecules on both ends and to amplify the amount of DNA in the library. According to one embodiment, the PCR is performed with one or more primers that anneal to the adapters. Respective amplification steps are well known in the prior art and thus, do not need any detailed description here. According to one embodiment, a size-selective DNA isolation according to the method of the present invention is performed after amplification. The cut-off value is again chosen such that primers, unligated adapter monomers and adapter-adapter ligation products that might have been present during amplification and might have been amplified, are not captured during DNA binding. Preferably, the same cut-off value is used as was used when performing a size selective DNA isolation after the adapter ligation step.

Thus, according to one embodiment, the method according to the present invention comprises amplifying size selected adapter ligated double stranded DNA molecules to provide an enriched sequencing library, wherein after amplification, a size selection step is performed which comprises
 a) contacting the amplified sample with a binding buffer which comprises a chaotropic salt and a buffering agent to provide a binding mixture and binding DNA molecules having a size above the cut-off value to a binding matrix which has a silicon containing surface, wherein the cut-off value for binding is determined by the pH value of the binding mixture;
 b) separating the bound DNA from the remaining sample;
 c) optionally washing the bound DNA; and
 d) optionally eluting the bound DNA from the binding matrix.

After amplification enrichment, which preferably is followed by a size selective DNA isolation according to the present invention, the sequencing library is ready for use. Optionally, the prepared sequencing library can be validated, quantified and/or quality controls can be performed to verify the size of the obtained adapter ligated fragments, respectively PCR enriched fragments.

Suitable methods for preparing sequencing libraries are also described in Metzker, 2011, Voelkerding, 2009, and WO12/003374.

According to one embodiment the present invention provides a method for preparing sequencing library that is suitable for massive parallel sequencing, wherein said method comprises
 A) fragmenting DNA and optionally end repairing the DNA fragments to provide a sample comprising blunt end DNA fragments of different sizes;
 B) optionally performing a step of isolating DNA having a fragment size above a certain cut-off value wherein said size selection step comprises
  a) contacting the sample with a binding buffer which comprises a chaotropic salt and a buffering agent to provide a binding mixture and binding DNA fragments having a size above the cut-off value to a binding matrix which has a silicon containing surface, wherein the cut-off value is determined by the pH value of the binding mixture;
  b) separating the bound DNA from the remaining sample;
  c) washing the bound DNA; and
  d) eluting the bound DNA from the binding matrix;
 C) performing an adapter ligation step to provide a sample comprising double-stranded DNA molecules that are flanked by adapters,
 D) isolating and thus separating adapter ligated double stranded DNA molecules from unligated adapter monomers and adapter-adapter ligation products based on the larger size of the adapter ligated double stranded DNA molecules wherein said size selection step comprises
  a) contacting the sample with a binding buffer which comprises a chaotropic salt and a buffering agent to provide a binding mixture and binding adapter ligated double stranded DNA molecules to a binding matrix which has a silicon containing surface, wherein under the used binding conditions adapter monomers and adapter-adapter ligation products substantially do not bind to the binding matrix and wherein the cut-off value is determined by the pH value of the binding mixture;
  b) separating the bound DNA from the remaining sample;
  c) washing the bound DNA; and
  d) eluting the bound DNA from the binding matrix;
 E) optionally amplifying adapter ligated double stranded DNA molecules;
 F) optionally performing a step of isolating amplification products having a size above a certain cut-off value wherein said size selection step comprises
  a) contacting the sample comprising the amplification products with a binding buffer which comprises a chaotropic salt and a buffering agent to provide a binding mixture and binding DNA molecules having a size above the cut-off value to a binding matrix which has a silicon containing surface, wherein the cut-off value is determined by the pH value of the binding mixture;
  b) separating the bound DNA from the remaining sample;
  c) washing the bound DNA; and
  d) eluting the bound DNA from the binding matrix.

Said method provides a sequencing library comprising adapter ligated DNA fragments having an appropriate minimal length. As discussed above, preferably, adapters are provided at the 3' end and the 5' end of the DNA fragments. Furthermore, the size selection step performed in step D) efficiently removes adapter monomers and adapter-adapter ligation products as well as other contaminants from the ligation reaction. This improves the quality of the sequencing library. Step D) can also be repeated and thus be performed two or more times in order to ensure an efficient removal of substantially all adapter monomers and adapter-adapter ligation products and to increase the size selection stringency. The method is fast, reliable and provides a sequencing library of high quality. Furthermore, said method can be easily integrated in existing sequencing library preparation methods.

A single NGS run usually produces enough reads to sequence several target enriched sequencing libraries at once. Therefore, pooling strategies and indexing approaches are a practical way to reduce the per sample cost. Respective multiplexing strategies can also be used in conjunction with the teaching of the present invention. Features enabling multiplexing can be incorporated in different stages of the enrichment process. According to one embodiment, the sequencing library is generated by using adaptors containing specific sequence motifs for library labelling and differentiation ("barcoded" or "index" adapters). Each sequencing library is provided with individual and thus library specific adapters which provide a library specific sequence. Preferably, each adapter comprises besides the index region a common universal region which provides a known template for PCR primers and/or sequencing primers that can be used on all libraries. After the target enriched sequencing libraries were obtained, they can be pooled and sequenced in a single run. Providing the DNA fragments of the sequencing library with respective index adaptors thus allows subsequently sequencing several target enriched sequencing libraries in the same sequencing run because the sequenced fragments can be distinguished based on the library specific sequence of the index adaptors. After sequencing, the individual sequences belonging to each library can be sorted via the library specific index which is then found in the obtained sequence. Respective index approaches are known in the prior art and index adapters are also commercially available and are for example provided in the TruSeq® DNA sample prep kits which are suitable for use in the Illumina platform.

According to one embodiment, the sequencing library comprises the double-stranded DNA molecules in an overall amount of 3 µg or less, 2 µg or less, 1.5 µg or less, 1 µg or less, 0.75 µg or less, 0.5 µg or less, 0.4 µg or less, 0.3 µg or less, 0.2 µg, 0.1 µg or less or 0.075 µg or less. The method according to the resent invention not only enables a size-selective DNA isolation based upon the pH value, that is used during binding, but also ensures an efficient capture of DNA molecules having the desired size. This is an important advantage, because in many cases, the sequencing library comprises the DNA in low amounts as DNA material might also get lost during the preparation of the sequencing library. The sequencing library may be prepared using 5 µg or less, 4 µg or less, 3 µg or less, 2 µg or less, 1.5 µg or less, 1 µg or less, 0.75 µg or less, 0.5 µg or less, 0.4 µg or less, 0.3 µg or less, 0.2 µg or less or 0.1 µg or less nucleic acid starting material.

Nucleic acids such as DNA and/or RNA can be isolated from a sample of interest according to methods known in the prior art to provide the starting material for preparing the sequencing library. RNA is usually first transcribed into cDNA prior to preparing the sequencing library.

As discussed above, sequencing is preferably performed on a next generation sequencing platform. All NGS platforms share a common technological feature, namely the massively parallel sequencing e.g. of clonally amplified or single DNA or cDNA molecules that are spatially separated in a flow cell or by generation of an oil-water emulsion. In NGS, sequencing is performed by repeated cycles of polymerase-mediated nucleotide extensions or, in one common format, by iterative cycles of oligonucleotide ligation. After obtaining the sequencing library using the method according to the present invention, clonal separation of single molecules and subsequent amplification is performed by in vitro template preparation reactions like emulsion PCR (pyrosequencing from Roche 454, semiconductor sequencing from Ion Torrent, SOLiD sequencing by ligation from Life Technologies, sequencing by synthesis from Intelligent Biosystems), bridge amplification on the flow cell (e.g. Solexa/Illumina), isothermal amplification by Wildfire technology (Life Technologies) or rolonies/nanoballs generated by rolling circle amplification (Complete Genomics, Intelligent Biosystems, Polonator). Sequencing technologies like Heliscope (Helicos), SMRT technology (Pacific Biosciences) or nanopore sequencing (Oxford Nanopore) allow direct sequencing of single molecules without prior clonal amplification. Suitable NGS methods and platforms that can be used were also described in the background of the present invention and it is referred to the respective disclosure. The sequencing can be performed on any of the respective platforms using a sequencing library prepared from a target RNA depleted composition obtained according to the teachings of the present invention. According to one embodiment, wherein the method of the present invention is used in order to remove unligated adapter monomers or adapter dimers, after sequencing the respectively obtained sequencing library, the reads for adapter-dimers relative to the number of total reads is ≤1.5%, preferably ≤1.25%, ≤1%, ≤0.75%, ≤0.6%, more preferred ≤0.5%, ≤0.4%, ≤0.3%, more preferred ≤0.2% and most preferred ≤0.15%. As is shown by the examples, the method according to the present invention achieves such a removal efficiency.

Kits

According to a further aspect, the present invention provides a kit for the selective binding of DNA molecules having a size above a desired cut-off value, comprising
  a) a binding buffer comprising a chaotropic salt and a buffering agent, wherein the binding buffer has a defined pH value that allows binding of DNA molecules having a size above a desired cut-off value when mixed with a DNA containing sample;
  b) a binding matrix having a silicon containing surface;
  c) optionally a washing solution; and
  d) optionally an elution solution.

Details regarding the binding buffer, in particular suitable and preferred binding buffer components, binding buffer component concentrations and pH values, as well as details regarding the binding matrix, the washing solution and the elution solution were described in detail above in conjunction with the method according to the present invention. It is referred to the above disclosure which also applies here. Non-limiting selected embodiments are again described subsequently.

Suitable and preferred concentrations for the chaotropic salt in the binding buffer were described above and it is referred to the above disclosure. Preferably, the concentration of chaotropic salt is at least 2.5M, more preferred at least 3M, more preferred at least 3.25M, most preferred at least 3.5M in the binding buffer. According to one embodiment, the chaotropic salt comprised in the binding buffer is a guanidinium salt. Suitable guanidinium salts were described above. Preferably, guanidinium (iso)thiocyanate is used.

Suitable buffering agents and concentrations in the binding buffer were described above and it is referred to the above disclosure which also applies here. Preferably, the buffering agent has a temperature stable pKa. Suitable and preferred embodiments were described above and it is referred to the above disclosure. Preferably, the buffering agent is MOPS. According to one embodiment, the binding buffer comprises a guanidinium salt, preferably guanidinium thiocyanate, in a concentration that is selected from the range 3M-5M, preferably, 3.25M to 4.5M and MOPS in a concentration that is selected from the range 100 mM to 400 mM, preferably 175 mM to 250 mM Preferably, the pH value of the binding buffer is selected from ≥7, ≥7.25, ≥7.5, ≥7.6, ≥7.7, 7.8 and ≥7.9. Suitable and preferred pH values and ranges of the binding buffer were also described above in conjunction with the method according to the present invention. It is referred to the respective disclosure which also applies here. As described above, preferably, the binding buffer has a pH value that lies in a range of 7 to 9.5, preferably 7.1 to 9.4, 7.2 to 9.3, 7.3 to 9.2, 7.4 to 9.1, 7.5 to 9.0, 7.6 to 8.9, 7.7 to 8.8, 7.8 to 8.7 and 7.9 to 8.6. According to one embodiment, the binding buffer has a pH value that lies in the range of 7.9 to 8.2, preferably 8.0 to 8.1. As is demonstrated by Example 1, such a binding buffer is particularly suitable for size selection when using guanidinium thiocyanate as gunaidinium salt.

According to one embodiment, the binding buffer comprises $CaCl_2$. $CaCl_2$ may be contained in a concentration of at least 2M, preferably at least 2.25M. The pH value may be selected from the range of 7 to 8, depending on the desired cut-off value. Suitable buffering agents were described above Suitable buffering agents were described above, MOPS being preferred for the above described reasons. According to one embodiment, MOPS is used in a concentration selected from the range of 50 mM to 200 mM, preferably 75 mM to 150 mM.

According to a preferred embodiment, the binding buffer does not comprise a binding enhancer selected from the group consisting of alcohols, polymers and detergents. According to one embodiment, the binding buffer does not comprise any other binding enhancer except for the chaotropic salt.

Suitable and preferred embodiments of the binding matrix were also described in conjunction with the method according to the invention. As described above, the binding matrix preferably provides an unmodified silica surface. Preferably, a column-based binding matrix is used.

According to one embodiment, the kit comprises at least one additional buffer which has a pH value different from the binding buffer. A respective additional buffer allows e.g. to flexibly adjust or chose the appropriate binding pH value according to the desired cut-off value. According to one embodiment, two or more respective additional buffers are comprised in the kit. According to one embodiment, said one or more additional buffer(s) is a binding buffer which differs in its pH value from the main binding buffer. According to one embodiment, the one or more additional buffer comprises a chaotropic salt. According to one embodiment, the kit comprises two or more binding buffers, e.g. in form of a set of binding buffers. According to one embodiment, said binding buffers have an identical composition but differ in their pH value and thus, provide different cut-off values when mixed with a DNA containing sample. According to one embodiment, the pH value of the binding buffers differ by at least 0.2 pH units, at least 0.3 pH units, at least 0.4 pH units, at least 0.5 pH units, at least 0.6 pH units, at least 0.7 pH units, at least 0.8 pH units, at least 0.9 pH units, at least 1.0 pH units, at least 1.1 pH units, at least 1.2 pH units, at least 1.3 pH units, at least 1.4 pH units or by at least 1.5 pH units. This also depends on the desired cut-off values that are supposed to be achieved with the binding buffers.

Furthermore, the kit may comprise instructions and/or information for use. E.g. the kit may comprise instructions and/or information regarding the cut-off value that is achieved when mixing a certain volume of the binding buffer with a certain volume of the DNA containing sample and/or the cut-off value(s) that are achieved if the DNA containing sample is mixed in a certain ratio with the binding buffer and one or more additional buffers comprised in the kit. Depending on the used volumes/ratios, different pH values can be adjusted in the binding mixture. If two or more binding buffers are comprised in the kit that differ in their pH value, the kit may provide information which cut-off value is achieved when using a certain binding buffer comprised in the kit. Thus, the present invention provides a kit which allows the flexible adjustment of the binding pH value by mixing a certain volume of the binding buffer and a certain volume of the one or more additional buffers having a pH value different from the binding buffer with the sample.

A respective kit can be in particular used in the method according to the first or second aspect. In particular, it can be used for fractionating DNA molecules comprised in a DNA containing sample according to their length.

This invention is not limited by the exemplary methods and materials disclosed herein, and any methods and materials similar or equivalent to those described herein can be used in the practice or testing of embodiments of this invention. Numeric ranges are inclusive of the numbers defining the range. The headings provided herein are not limitations of the various aspects or embodiments of this invention which can be read by reference to the specification as a whole.

The term "solution" as used herein in particular refers to a liquid composition, preferably an aqueous composition. It may be a homogenous mixture of only one phase but it is also within the scope of the present invention that a solution comprises solid constituents such as e.g. precipitates.

According to one embodiment, subject matter described herein as comprising certain steps in the case of methods or as comprising certain ingredients in the case of compositions, solutions and/or buffers refers to subject matter consisting of the respective steps or ingredients. It is preferred to select and combine preferred embodiments described herein and the specific subject-matter arising from a respective combination of preferred embodiments also belongs to the present disclosure.

The present application claims priority of prior applications U.S. 61/762,674 filed on Feb. 8, 2013 and EP 13 154 732.5, filed on Feb. 8, 2013 the entire disclosures of which are incorporated herein by reference.

EXAMPLES

Example 1: Size Selective Removal of DNA-Fragments from Sheared Genomic DNA

DNA was sheared with the Covaris ultrasonicator in TE buffer to provide a DNA containing sample. 1 volume DNA sample (90 μl) was mixed with 4 volumes of a binding buffer to provide a binding mixture. 3 different binding buffers were tested:
Binding buffer A: 3.5M GTC, 200 mM MOPS, pH 7.4
Binding buffer B: 3.5M GTC, 200 mM MOPS, pH 7.8
Binding buffer C: 3.5M GTC, 200 mM MOPS, pH 8.0

As can be seen, the binding buffers A to C only differed in their pH value. The obtained binding mixture was spun through a column comprising a silica membrane as binding matrix (QIAquick MinElute spin column (QIAGEN)). The column was washed twice with 80% Ethanol and the DNA was eluted with an elution buffer (10 mM Tris-Cl, pH 8.5).

The eluates obtained with the binding buffers A to C were analyzed on an Agilent 7500 Chip in order to analyse the cut-off values achieved with the used binding buffers. The results are shown in FIG. 1. The large peaks shown at 50 bp and 10,380 bp result from the calibration markers. The curve between the markers resembles the DNA fragments of different sizes that were isolated with the different binding buffers. Thus, the curve inbetween the calibration markers shows the size distribution of the isolated DNA fragments. As can be seen, at pH 7.4 a cut-off value of approx. 50 bp was achieved, i.e. only fragments having a size of 50 bp or above were bound to the column under the used binding conditions. At pH 7.8, the cut-off value was approx. 100 bp. At pH 8.0, the cut-off value was approx. 150 bp. Example 1 accordingly demonstrates that a variation in the pH value influences the cut-off value and accordingly, enables a size selective isolation of DNA fragments. A higher pH value increased the cut-off value. Therefore, a variation in the pH value allows to precisely adjust the cut-off value for size selection by determining the size of the DNA molecules that can bind to the binding matrix.

Example 2: Illumina TruSeq Library Preparation Using Prior Art Methods or the Invention for Size Selection The size selection method according to example 1 was compared with AmPure beads (Beckman-Coulter) based DNA isolation in a TruSeq DNA library preparation workflow for next generation sequencing. DNA from *Bacillus subtilis* was processed according to the TruSeq DNA Sample Preparation Guide v2 (Illumina) using AMPure beads as described in the handbook (prior art) or by replacing the described AMPure purification steps completely by the method according to the invention (see example 1, using binding buffer C) in order to achieve a cut-off value of 150 bp. A cut-off value of 150 bp is favourable, as adapter monomers (approx. 60 bp) and adapter dimers (approx. 120 bp) can be efficiently removed during size selection. No size selection via gel purification was performed, i.e. size selection of DNA was exclusively performed by using either the AMPure beads based isolation protocol described in the handbook or by using the method according to the present invention as described in example 1, using binding buffer C. A size selection was performed at two points of the sequencing library preparation. The first size selection was performed after DNA fragmentation and end-repair of the fragmented DNA, the second size selection was performed after adapter ligation in order to remove unligated adapter monomers and adapter dimers. The results are shown in FIGS. 2 to 4.

Figure 2:
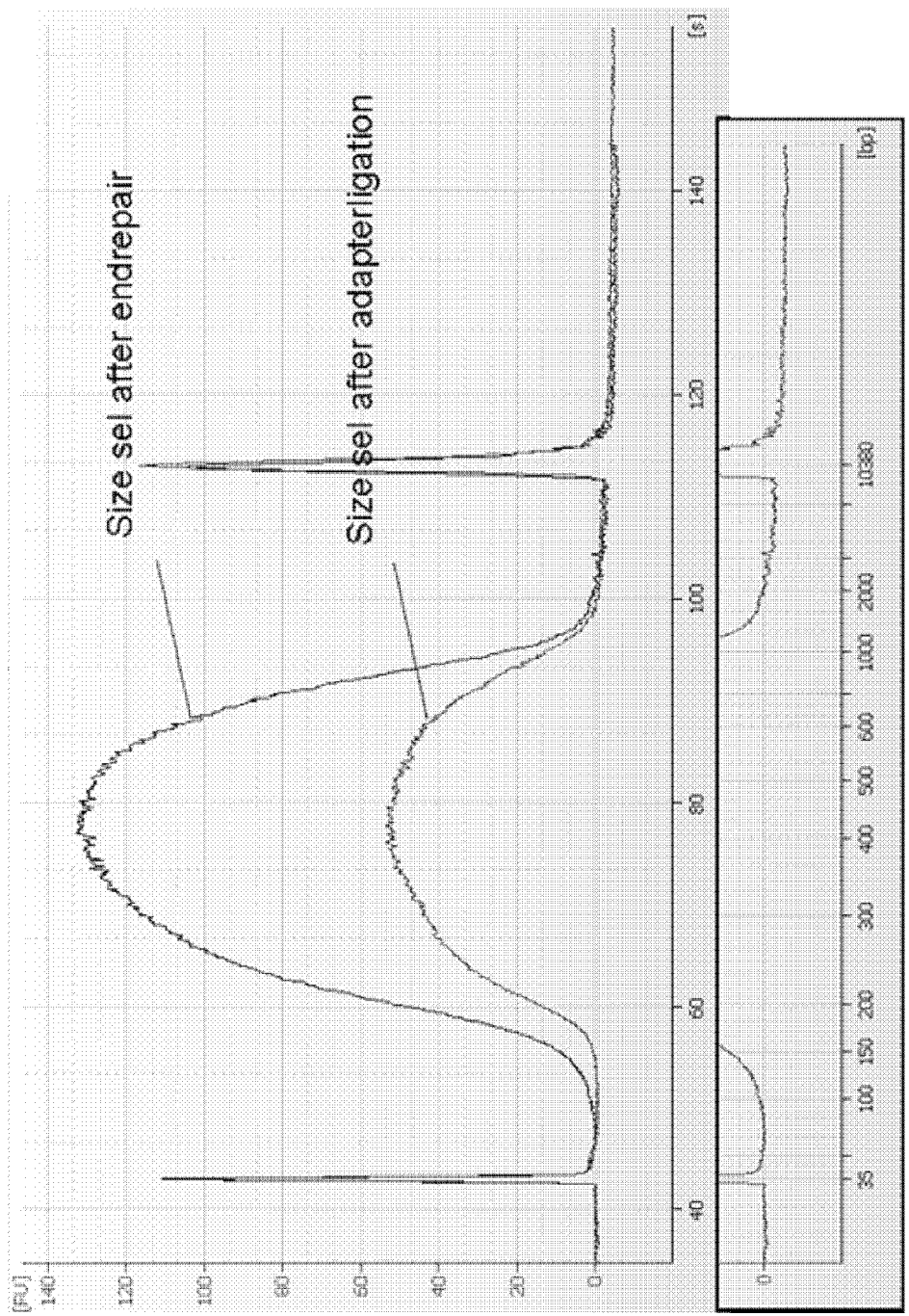
Figure 3:
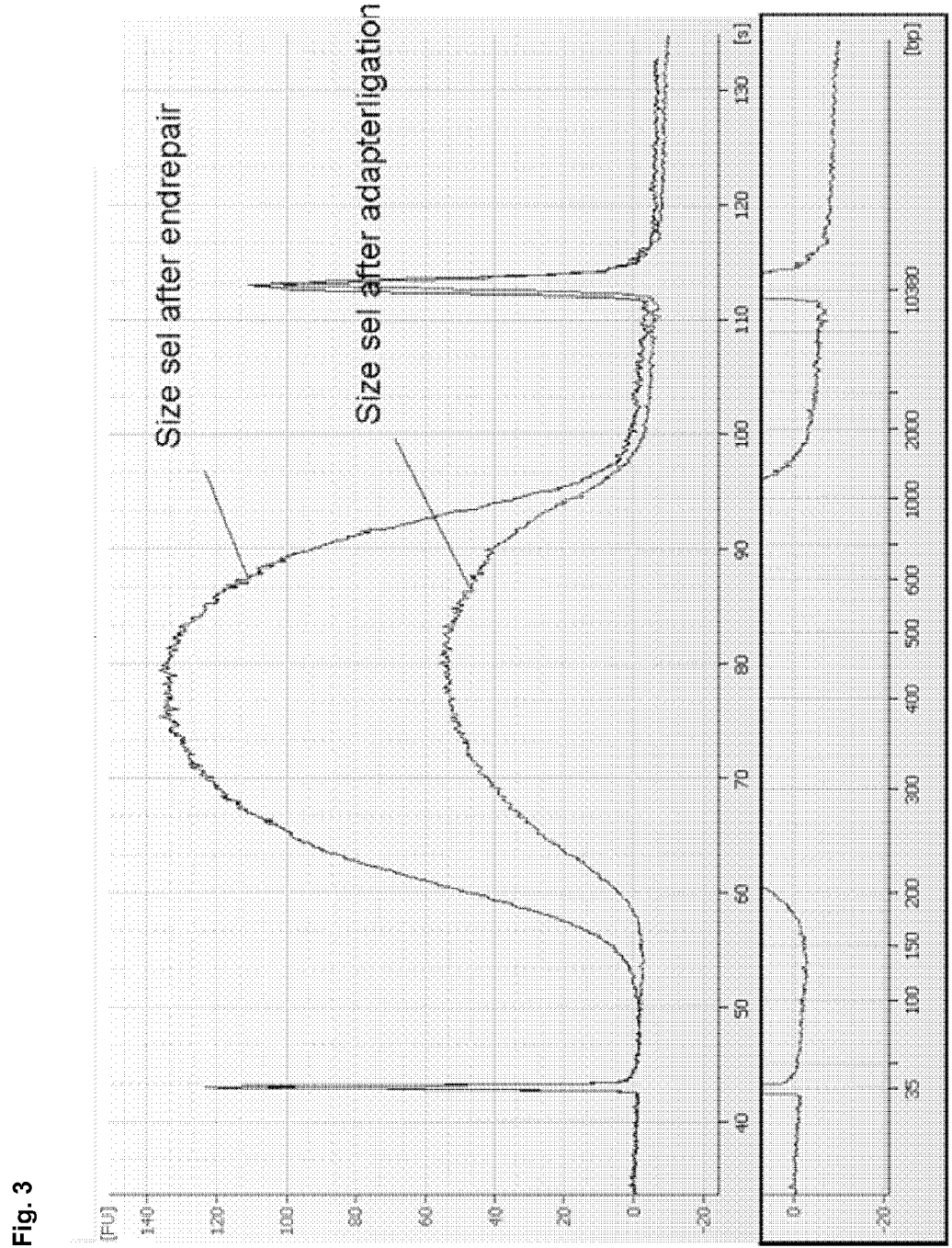
Figure 4:
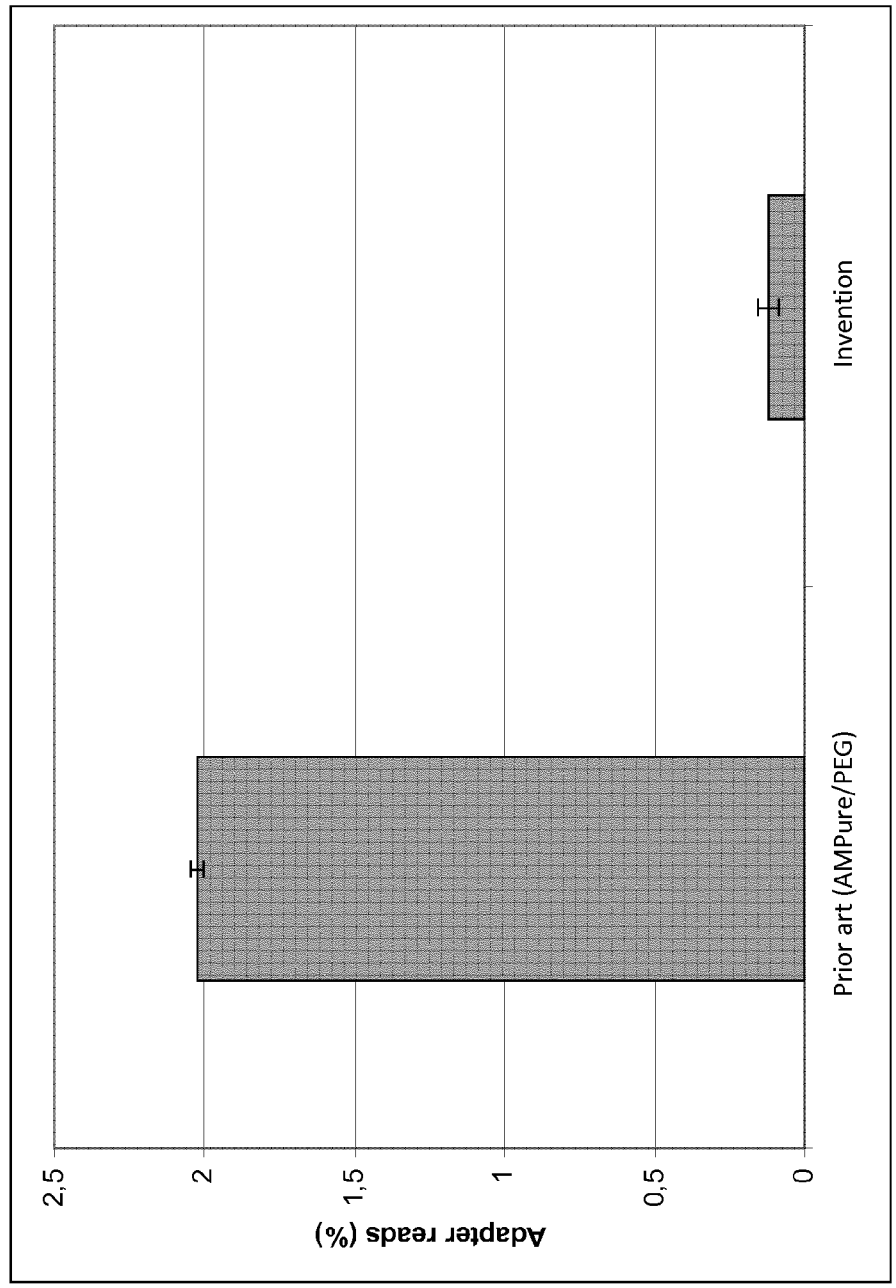

In FIG. 2 (invention) and FIG. 3 (AMPure beads), the size distribution of the DNA fragments obtained after size selection of the end-repaired DNA fragments and after size selection following adapter ligation was compared. As can be seen, both methods are suitable to remove small DNA fragments and in particular are suitable to remove adapter monomers and adapter dimers. The increase in the size of the DNA fragments due to correct adapter ligation is evident from FIGS. 2 and 3. FIGS. 2 and 3 demonstrate comparable results with regard to yield and distribution.

After sequencing of three different libraries per size selection method, the reads for adapters-dimers were calculated relative to the number of total reads. Thereby, it was determined which method was more effective in removing unwanted adapter dimers from the sequencing library. The results are shown in FIG. 4. As can be seen, the method according to the present invention provided significantly lower amounts of adapter reads which demonstrates that the present invention was more effective in removing unligated adapters and adapter-adapter ligation products having a size below the cut-off value than the standard prior art method. Because of its efficiency, the present invention also makes cumbersome gel separation based size selection steps obsolete. Therefore, besides the significantly faster and more convenient protocol, the size selection according to the invention also showed a better adapter removal efficiency than the standard prior art method.

The bead based AMPure system of the prior art and the column-based size selection according to the invention were also compared side-by-side to determine the time needed for completing the size selective DNA purification. One cycle of size selection according to the method of the present invention can be completed in less than 10 min if desired, while the prior art AMPure bead based method requires at least about approx. 1 hour in order to complete one size selection cycle. Therefore, the method according to the present invention is considerably faster. For several applications, in particular for adapter removal, it is preferred to perform two cycles of size selection in order to ensure that the adapter monomers and adapter-adapter ligation products are efficiently removed. This is beneficial because adapters are used in large excess during adapter ligation. E.g. two consecutive size selection steps are recommended in the the TruSeq DNA Sample Preparation Guide v2 (Illumina) for adapter removal. Here, two cycles of size selection according to the present invention can be completed in less than 20 min, while the AMPure bead based prior art method requires approx. 120 min. Therefore, the time saving that is achieved with the method according to the present invention is particularly prominent, if more than one size selection cycle is performed, as the time savings add up. Furthermore, the method of the invention is suitable for automation.

Figure 5A:
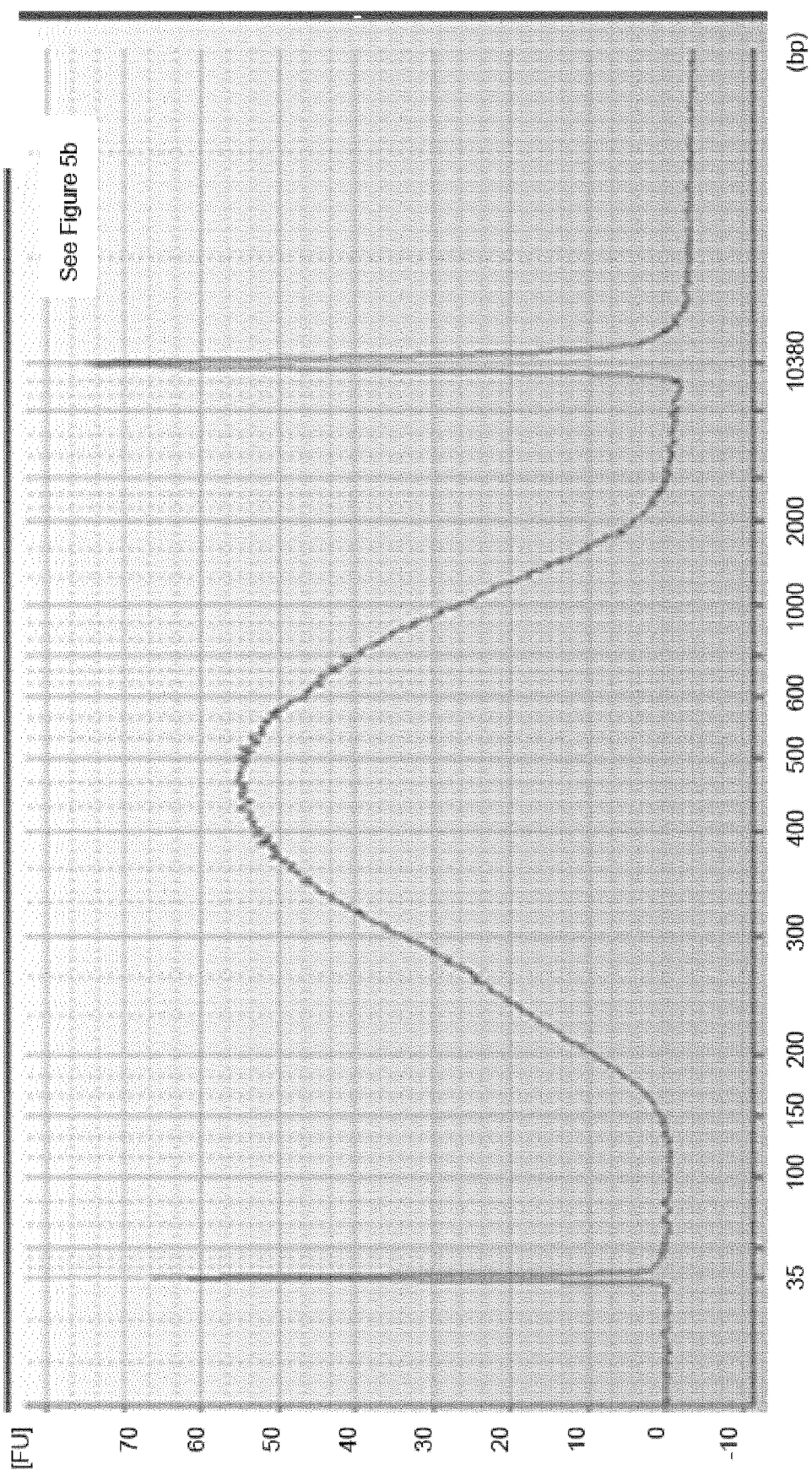
Figure 5B:
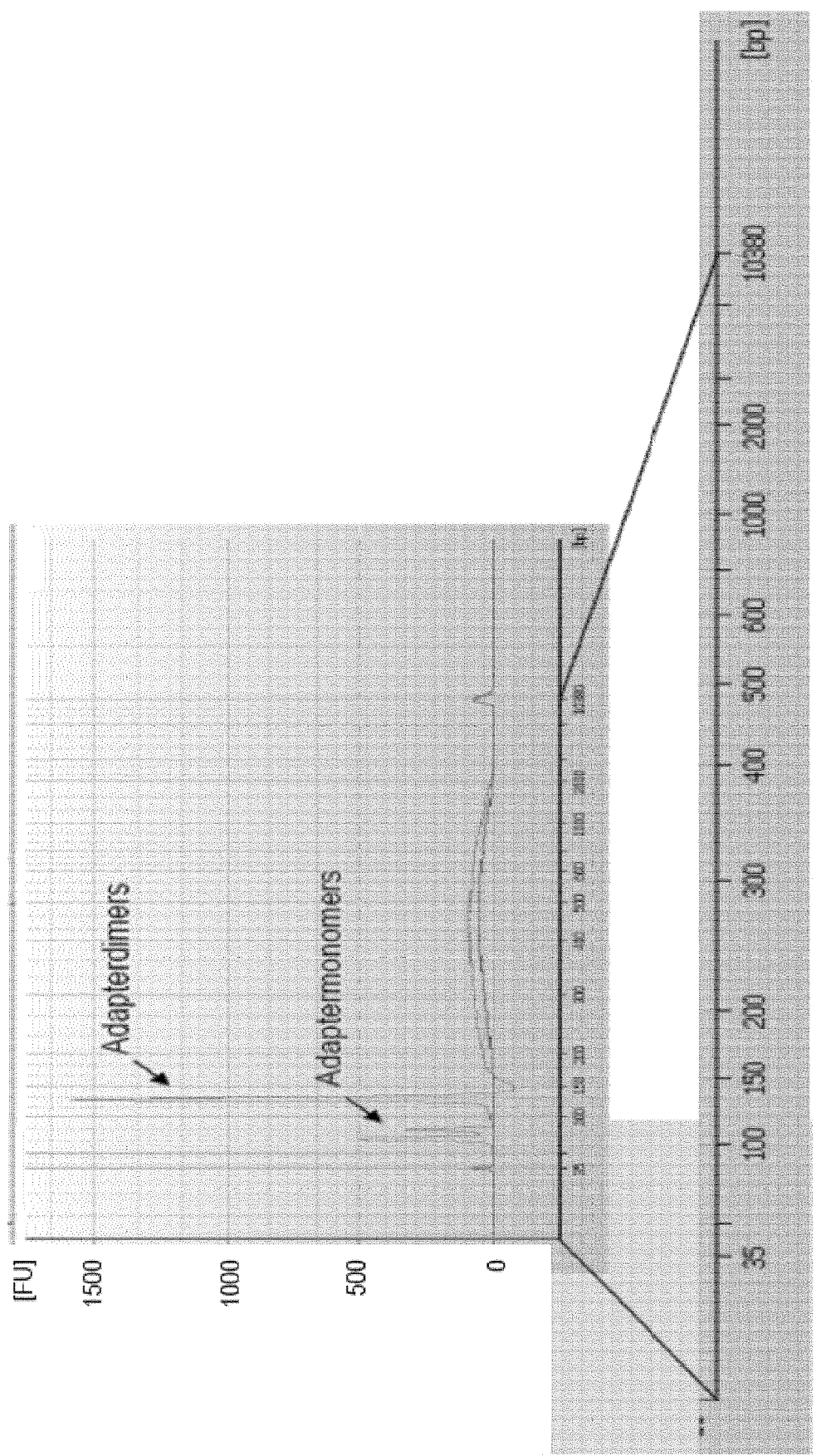

FIG. 5 demonstrates the results that are obtained if no adapter removal step based on size selection according to the present invention is performed. The large image shows the unpurified adapter ligated library. As can be seen, the adapter monomers and the adapter dimers provide prominent peaks. The small image shows again the results that are obtained with the method of the invention, wherein adapter monomers and adapter dimers are removed by size selection.

Example 3: Size Selection Using a Different Binding Buffer

As DNA containing sample, 30 µl of a DNA molecular weight marker (Gel Pilot 1 kb ladder, QIAGEN) in a total volume of 100 µl was used as sample input material for each size selection. Three different binding buffers were tested:
Binding buffer D: 3.5M GITC, sodium citrate, pH 7
Binding buffer E: 3.5M GITC, sodium citrate, pH 8
Binding buffer F: 3.5M GITC, sodium citrate, pH 9.

Figure 6:
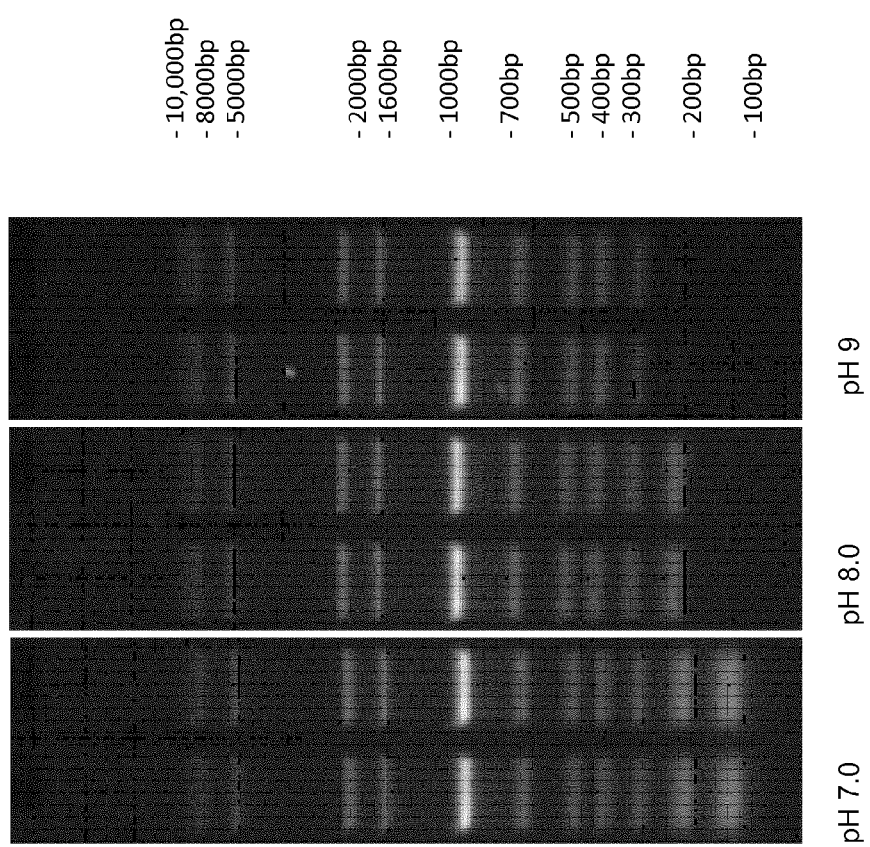
FIG. 6 shows the increasing cut-off in binding to a glass-fiber matrix with increasing pH value of the binding buffer which comprises a chaotropic salt and a buffering agent (see example 3).

DNA was then isolated as described in example 1. The results are shown in FIG. 6. 10 µl of the eluate were used for gel electrophoresis (1% agarose-gel in buffer TAE). As can be seen, when increasing the pH stepwise, there is a shift in bound fragments in that way that fragments <200 (pH 8) and <300 bp (pH 9) were not bound. Thus, increasing the binding pH value increased the cut-off value so that only larger DNA fragments were bound. Therefore, a precise size selection was again possible by precise adjustment of the binding pH value. By changing the pH-value in smaller steps, a completely variable size selection of a given DNA-fraction is possible.

Example 4: Size Selective Removal of DNA Fragments with Unmodified Magnetic Silica Beads in pH-Dependent Matter 30 µl of a DNA Molecular Weight Marker (Gel Pilot 1 kb ladder, QIAGEN) in a total volume of 100 µl were mixed with 10 µl magnetic silica bead suspension (MagAttract Suspension G, QIAGEN).

200 µl of a binding buffer was added. Two different binding buffers were used:
Binding buffer G: 3.5M GITC, sodium citrate, pH 7
Binding buffer H: 3.5M GITC, sodium citrate, pH 7.5

The binding mixture was incubated with the beads for 10 min under constant shaking. Beads were separated with a magnetic rack for 1 min and the supernatant was removed.

The beads with the bound DNA were washed two times with Buffer PE (QIAGEN) for 5 min each with constant shaking, separated and the supernatant removed. After air-drying for 15 min to remove residual ethanol, the bound DNA was eluted by mixing with 55 µl elution buffer (Buffer EB, QIAGEN) for 5 min at room temperature. After separation of the beads, 50 µl of the eluate were removed and used for further analysis.

10 µl of the eluate were used for gel electrophoresis (1% agarose-gel in buffer TAE). The results are shown in FIG. 7. As can be seen, binding buffer G (pH 7.0) allowed to recover all DNA fragments having a length from 100 bp to 10 kb. Binding buffer H (pH 7.5) allowed to recover DNA fragments having a size ≥700 bp. Smaller fragments were depleted as can be derived from FIG. 7. This demonstrates that the chaotropic pH-adjustable size selection according to the invention is also suitable with non-functionalized magnetic silica beads.

Example 5: Size Selective Removal of DNA-Fragments from Sheared Genomic DNA Using Guanidinium Hydrochloride and CaCl₂

90 µl of a sample containing 1 µg sheared DNA was prepared as described in example 1. 1 volume DNA sample (90 µl) was mixed with 4 volumes of a binding buffer to provide a binding mixture. The following binding buffers were tested:
Binding buffer I: 3.5M GuHCl, 200 mM MOPS, pH 7
Binding buffer J: 3.5M GuHCl, 200 mM MOPS, pH 7.3
Binding buffer K: 3.5M GuHCl, 200 mM MOPS, pH 8
Binding buffer L: 2.5M CaCl₂, 200 mM MOPS, pH 7
Binding buffer M: 2.5M CaCl₂, 200 mM MOPS, pH 7.3
Binding buffer N: 2.5M CaCl₂, 200 mM MOPS, pH 8

As can be seen, binding buffers I to K and L to N only differed in their pH value. The pH of binding buffers was adjusted to the value indicated by NaOH addition. The obtained binding mixture was spun through a column comprising a silica membrane as binding matrix (QIAquick MinElute spin column (QIAGEN)). The column was washed twice with 80% Ethanol and the DNA was eluted with an elution buffer (10 mM Tris-Cl, pH 8.5).

The eluates obtained with the binding buffers I to N were analyzed using the Bioanalyzer, the Chip DNA 7500 series II and the software 2100 Expert (version B02.08 SI 648) from Agilent in order to analyse the cut-off values achieved with the different binding buffers. The results are summarized in the below Table 1:

TABLE 1

| Binding buffer | Cut-off value |
|---|---|
| I | 74 bp |
| J | 89 bp |
| K | >1000 bp |
| L | >1000 bp |
| M | 92 bp |
| N | 50 bp |

Again, also the results from Example 5 demonstrate that a variation in the pH value influences the cut-off value and accordingly, enables a size selective isolation of DNA fragments. A higher pH value increased the cut-off value in case of GuHCl. The binding buffer containing CaCl₂ size-selected the DNA in opposite orientation. Here, the higher the pH value, the lower the cut-off value. However, both chaotropic cations resulted in pH dependent size selection.

The invention claimed is:

1. A method for isolating DNA molecules having a size above a certain cut-off value from a DNA containing sample, comprising
    a) contacting the sample with a binding buffer which comprises a chaotropic salt and a buffering agent to provide a binding mixture, and binding DNA molecules having a size above the cut-off value to a binding matrix which has a silicon containing surface,
    wherein the binding mixture has a pH value in a range of 7 to 9.5 and comprises the chaotropic salt in a concentration range of 2M to 4.25M,
    wherein the cut-off value is determined by the pH value of the binding mixture, and
    wherein the binding is performed in the absence of an alcohol;
    b) separating the bound DNA from the remaining sample;
    c) optionally washing the bound DNA; and
    d) optionally eluting the bound DNA from the binding matrix.

2. The method of claim 1, wherein the method is for isolating adapter ligated DNA molecules from an adapter ligation sample and for removing adapter monomers and adapter-adapter ligation products, wherein adapter ligated DNA molecules are separated from unligated adapter monomers and adapter-adapter ligation products based on the larger size of the adapter ligated DNA molecules, and wherein step a) comprises
    contacting the adapter ligation sample with the binding buffer to provide a binding mixture and binding adapter ligated DNA molecules to the binding matrix, wherein under the used binding conditions adapter monomers and adapter-adapter ligation products substantially do not bind to the binding matrix.

3. The method according to claim 1, wherein the chaotropic salt is a guanidinium salt.

4. The method according to claim 1, wherein the chaotropic salt is present in the binding mixture and/or in the binding buffer in a concentration range selected from 2.25M to 4M, 2.5M to 3.75M, and 2.75M to 3.5M.

5. The method according to claim 1, wherein the buffering agent has a temperature stable pKa.

6. The method according to claim 5, wherein the buffering agent is MOPS.

7. The method according to claim 1, wherein the binding conditions are exclusively established by the binding buffer.

8. The method according to claim 1, wherein after contacting the binding buffer with the DNA containing sample, a binding pH value is provided in the resulting binding mixture that corresponds to or substantially corresponds to the pH value of the binding buffer and/or wherein the pH value in the binding mixture does not deviate by more than +/−0.2 pH units from the pH value of the binding buffer.

9. The method according to claim 1, wherein a binding pH value is used which sets the cut-off value in a range selected from 100 nt to 350 nt, 110 nt to 325 nt, 115 nt to 300 nt, 120 nt to 275 nt, 125 nt to 250 nt, 130 nt to 225 nt, 135 nt to 200 nt, 140 nt to 190 nt, 145 nt to 180 nt, 145 nt to 170 nt and 150 nt to 160 nt.

10. The method according to claim 1, wherein the binding buffer and/or the binding mixture has a pH value range selected from 7.25 to 9.5, 7.5 to 9.5, 7.6 to 9.5, 7.7 to 9.5, 7.8 to 9.5, and 7.9 to 9.5.

11. The method according to claim 1, wherein the binding mixture and/or the binding buffer comprises a guanidinium salt and a buffering agent having a temperature stable pKa, and wherein the binding mixture and/or the binding buffer has a pH value range selected from 7.5 to 9.5, 7.6 to 9.5, and 7.7 to 9.5.

12. The method according to claim 11, wherein the binding buffer is an aqueous solution comprising or consisting of
a guanidinium salt in a concentration range 2.5M to 4.5M, and
a temperature stable buffering agent in a concentration that is selected from 100 mM to 400 mM.

13. The method according to claim 1, wherein the pH value of the binding buffer and/or the binding mixture lies in a range from 7.1 to 9.4, 7.2 to 9.3, 7.3 to 9.2, 7.4 to 9.1, 7.5 to 9.0, 7.6 to 8.9, 7.7 to 8.8, 7.8 to 8.7 and 7.9 to 8.6.

14. The method according to claim 13, wherein
i) the binding mixture and/or the binding buffer has a pH value of 7.9 to 8.1 and wherein the cut-off value lies in the range of 125 nt to 170 nt; or
ii) the binding mixture and/or the binding buffer has a pH value of 7.6 to 7.8, wherein the cut-off value lies in the range of 80 nt to 120 nt.

15. The method according to claim 11, wherein the guanidinium salt is guanidinium thiocyanate.

16. The method according to claim 1, wherein at least two size selective purification cycles comprising steps a) to d) are performed.

17. The method according to claim 1, wherein the binding matrix provides a silica surface for DNA binding.

18. The method according to claim 1, wherein the binding matrix is comprised in a column.

19. The method according to claim 1, wherein the DNA molecules are linear, double-stranded DNA molecules.

20. The method according to claim 1, wherein the DNA containing sample has one or more of the following characteristics:
i) the DNA containing sample is a sample of extracted DNA or extracted DNA that has been further processed;
ii) the DNA containing sample was obtained after an enzymatic reaction;
iii) the DNA containing sample comprises fragmented DNA;
iv) the DNA containing sample comprises linear, blunt-ended DNA fragments of different sizes;
v) the DNA containing sample comprises amplification products;
vi) the DNA containing sample is an adapter ligation sample that was obtained as a result of an adapter ligation step; and
vii) the DNA containing sample is an adapter ligation sample which comprises (i) double-stranded DNA molecules that are flanked 5' and/or 3' by adapters, (ii) adapter monomers and (iii) adapter-adapter ligation products.

21. The method according to claim 1, wherein the DNA containing sample was obtained during the preparation of a sequencing library.

22. The method according to claim 2, wherein the cut-off value lies above the size of adapter monomers and above the size of expected adapter-adapter ligation products.

23. The method according to claim 2, wherein the isolated, size selected adapter ligated double-stranded DNA molecules are amplified to provide an enriched sequencing library, wherein after amplification, a size selection step is performed which comprises
a) contacting the amplified sample with a binding buffer which comprises a chaotropic salt and a buffering agent to provide a binding mixture and binding DNA molecules having a size above the cut-off value to a binding matrix which has a silicon containing surface, wherein the cut-off value for binding is determined by the pH value of the binding mixture;
b) separating the bound DNA from the remaining sample;
c) optionally washing the bound DNA; and
d) optionally eluting the bound DNA from the binding matrix.

24. The method according to claim 1, for preparing a sequencing library that is suitable for massive parallel sequencing, wherein said method comprises
A) fragmenting DNA and optionally end repairing DNA fragments to provide a sample comprising blunt end DNA fragments of different sizes;
B) optionally performing a step of isolating DNA having a fragment size above a certain cut-off value, wherein said size selection step comprises
a) contacting the sample with a binding buffer which comprises a chaotropic salt and a buffering agent to provide a binding mixture and binding DNA fragments having a size above the cut-off value to a binding matrix which has a silicon containing surface, wherein the cut-off value is determined by the pH value of the binding mixture;
b) separating the bound DNA from the remaining sample;
c) washing the bound DNA; and
d) eluting the bound DNA from the binding matrix;
C) performing an adapter ligation step to provide a sample comprising double-stranded DNA molecules that are flanked 5' and/or 3' by adapters,
D) isolating and thus separating adapter ligated double-stranded DNA molecules from unligated adapter monomers and adapter-adapter ligation products based on the larger size of the adapter ligated double stranded DNA molecules wherein said size selection step comprises
a) contacting the sample with a binding buffer which comprises a chaotropic salt and a buffering agent to provide a binding mixture and binding adapter ligated double-stranded DNA molecules to a binding matrix which has a silicon containing surface, wherein under the used binding conditions adapter monomers and adapter-adapter ligation products substantially do not bind to the binding matrix and wherein the cut-off value is determined by the pH value of the binding mixture;
b) separating the bound DNA from the remaining sample;
c) washing the bound DNA; and
d) eluting the bound DNA from the binding matrix;
E) optionally amplifying adapter ligated double stranded DNA molecules;
F) optionally performing a step of isolating amplification products having a size above a certain cut-off value wherein said size selection step comprises
a) contacting the sample comprising the amplification products with a binding buffer which comprises a chaotropic salt and a buffering agent to provide a binding mixture and binding DNA molecules having a size above the cut-off value to a binding matrix which has a silicon containing surface, wherein the cut-off value is determined by the pH value of the binding mixture;
b) separating the bound DNA from the remaining sample;
c) washing the bound DNA; and
d) eluting the bound DNA from the binding matrix.

25. The method according to claim 1, wherein binding is performed in the absence of binding enhancers selected from the group consisting of alcohols, polymers and detergents.

26. The method according to claim 1, having one or more of the following characteristics:
a) wherein the binding buffer does not comprise a binding enhancer selected from the group consisting of alcohols, polymers and detergents;
b) wherein binding is performed in the presence of the chaotropic salt and the buffering agent, but wherein no further binding enhancers are present in the binding mixture;
c) wherein the sample is not lysed or degraded prior to step a); and
d) wherein no additional agents are added to the DNA containing sample to prepare the binding mixture, except for the binding buffer.

27. The method according to claim 1, wherein the binding matrix has an unmodified silica surface.

28. The method according to claim 1, wherein the method is for fractionating DNA molecules comprised in a DNA containing sample according to their length.

29. The method according to claim 28, wherein two or more size selective DNA isolation cycles comprising steps a) to d) are performed, wherein
in the first size selective DNA isolation cycle, a first binding pH value is provided in the binding mixture of the first size selective DNA isolation cycle which determines a first cut-off value, and wherein the obtained eluate of the first size selective DNA isolation cycle provides a fraction which predominantly comprises DNA molecules having a size above the first cut-off value; and
the separated remaining sample obtained in step b) of the first size selective DNA isolation cycle provides a DNA containing sample for the second size selective DNA isolation cycle, a second binding pH value is provided in the binding mixture of the second size selective DNA isolation cycle which determines a second cut-off value, the second cut-off value is smaller than the first cut-off value, and the obtained eluate of the second size selective DNA isolation cycle provides a fraction which predominantly comprises DNA molecules having a size above the second cut-off value but below the first cut-off value.

30. The method according to claim 29, wherein the first pH value is higher than the pH value.

31. The method according to claim 28, wherein size fractionation comprises performing
a first size selective DNA isolation cycle comprising steps a) to d), wherein a first binding pH value is provided in a binding mixture of the first size selective DNA isolation cycle which determines a first cut-off value, and wherein the obtained eluate of the first size selective DNA isolation cycle provides a fraction which predominantly comprises DNA molecules having a size above the first cut-off value; and
a second size selection DNA isolation cycle comprising steps a) to d), wherein the separated remaining sample obtained in step b) of the first size selective DNA isolation cycle provides a binding mixture for a second size selective DNA isolation cycle, the pH value of the binding mixture for the second size selective DNA isolation cycle is adjusted to a second binding pH value which determines a second cut-off value, and the second cut-off value is smaller than the first cut-off value; thereby providing an eluate of the second size selectin DNA isolation cycle which predominantly comprises DNA molecules having a size above the second cut-off value but below the first cut-off value.

32. The method according to claim 1, wherein the method comprises providing a set of two or more binding buffers, wherein each binding buffer comprised in the set comprises a chaotropic salt and a buffering agent, and wherein each binding buffer has a different pH value and provides a different, defined pH value and thus cut-off value in the binding mixture.

33. The method according to claim 32, wherein from said set of binding buffers a binding buffer is chosen, which provides the desired cut-off value by establishing the appropriate binding pH value in the binding mixture, and wherein the binding buffers comprised in the set comprise the same chaotropic salt in the same concentration.

34. The method according to claim 2, wherein the method of the present invention is used in order to remove unligated adapter monomers or adapter dimers from a sequencing library, and wherein after sequencing the respectively obtained sequencing library, the reads for adapter-dimers relative to the number of total reads is ≤1.5%.

35. The method according to claim 1, wherein the chaotropic salt is $CaCl_2$.

36. The method according to claim 1, wherein after contacting the binding buffer with the DNA containing sample, a binding pH value is provided in the resulting binding mixture that corresponds to or substantially corresponds to the pH value of the binding buffer and/or wherein the pH value in the binding mixture does not deviate by more than +/−0.15 pH units from the pH value of the binding buffer.

37. The method according to claim 1, wherein after contacting the binding buffer with the DNA containing sample, a binding pH value is provided in the resulting binding mixture that corresponds to or substantially corresponds to the pH value of the binding buffer and/or wherein the pH value in the binding mixture does not deviate by more than +/−0.1 pH units from the pH value of the binding buffer.

38. The method according to claim 1, wherein after contacting the binding buffer with the DNA containing sample, a binding pH value is provided in the resulting binding mixture that corresponds to or substantially corresponds to the pH value of the binding buffer and/or wherein the pH value in the binding mixture does not deviate by more than +/−0.05 pH units from the pH value of the binding buffer.

39. The method according to claim 1, wherein the DNA containing sample has one or more of the following characteristics:
   i) the DNA containing sample is a sample of extracted DNA or extracted DNA that has been further processed by shearing or by way of an enzymatic reaction;
   ii) the DNA containing sample was obtained after an amplification reaction or ligase reaction;
   iii) the DNA containing sample comprises sheared DNA;
   iv) the DNA containing sample comprises linear, blunt-ended DNA fragments of different sizes;
   v) the DNA containing sample comprises PCR amplification products;
   vi) the DNA containing sample is an adapter ligation sample that was obtained as a result of an adapter ligation step; and
   vii) the DNA containing sample is an adapter ligation sample which comprises (i) double-stranded DNA molecules that are flanked 5' and/or 3' by adapters, (ii) adapter monomers and (iii) adapter dimers.

40. The method according to claim 39, wherein the DNA containing sample was obtained after an adapter ligation reaction.

41. The method according to claim 5, wherein the buffering agent having a temperature stable pKa is selected from MOPS, PIPES, MOPSO, BES, HEPES, DIPSO, HEPPSO, POPSO, HEPPS, phosphate containing buffering agents, and carboxylic acid based buffering agents.

42. The method according to claim 22, wherein the cut-off value lies at least 10 nt, at least 15 nt, at least 20 nt, at least 25 nt or at least 30 nt above the size of expected adapter-adapter ligation product(s).

43. The method according to claim 33, wherein the pH value of the binding buffers differs between two binding buffers by at least 0.1 pH units, at least 0.2 pH units, at least 0.3 pH units, at least 0.4 pH units, at least 0.5 pH units, at least 0.6 pH units, at least 0.7 pH units, at least 0.8 pH units, at least 0.9 pH units, at least 1.0 pH units, at least 1.1 pH units, at least 1.2 pH units, at least 1.3 pH units, at least 1.4 pH units or by at least 1.5 pH units.

* * * * *

UNITED STATES PATENT AND TRADEMARK OFFICE
CERTIFICATE OF CORRECTION

PATENT NO. : 10,745,686 B2
APPLICATION NO. : 14/764045
DATED : August 18, 2020
INVENTOR(S) : Tanya Sperling et al.

Page 1 of 1

It is certified that error appears in the above-identified patent and that said Letters Patent is hereby corrected as shown below:

In the Claims

Column 40, Claim 30, Line 5:
"higher than the pH value." should read: -- higher than the second pH value. --.

Column 40, Claim 31, Line 16:
"a second size selection DNA isolation cycle" should read: -- a second size selective DNA isolation cycle --.

Column 40, Claim 31, Lines 25 and 26:
"the second size selectin DNA isolation cycle" should read: -- the second size selective DNA isolation cycle --.

Signed and Sealed this
Twenty-second Day of December, 2020

Andrei Iancu
*Director of the United States Patent and Trademark Office*